(12) United States Patent
Morzycki et al.

(10) Patent No.: US 8,552,161 B2
(45) Date of Patent: Oct. 8, 2013

(54) SAPONIN COMPOUNDS, METHODS OF PREPARATION THEREOF, USE THEREOF AND PHARMACEUTICAL COMPOSITIONS

(75) Inventors: Jacek Witold Morzycki, Bialystok (PL); Agnieszka Wojtkielewicz, Bialystok (PL); Jana Oklestkova, Olsany u Prostejova (CZ); Lucie Hoffmannova, Pribor (CZ); Miroslav Strnad, Olomouc (CZ)

(73) Assignees: Uniwersytet W Bialymstoku, Bialystok (PL); Univerzita Palackeho V Olomouci, Olomouc (CZ); Bioapex, S.R.O., Olomouc (CZ)

(*) Notice: Subject to any disclaimer, the term of this patent is extended or adjusted under 35 U.S.C. 154(b) by 118 days.

(21) Appl. No.: 13/147,771

(22) PCT Filed: Feb. 8, 2010

(86) PCT No.: PCT/CZ2010/000012
§ 371 (c)(1),
(2), (4) Date: Sep. 9, 2011

(87) PCT Pub. No.: WO2010/088866
PCT Pub. Date: Aug. 12, 2010

(65) Prior Publication Data
US 2011/0311652 A1   Dec. 22, 2011

(30) Foreign Application Priority Data
Feb. 9, 2009  (PL) .......................... 387235

(51) Int. Cl.
*C07J 41/00*  (2006.01)
*A01N 45/00*  (2006.01)

(52) U.S. Cl.
USPC ............................................. 536/5; 514/26

(58) Field of Classification Search
None
See application file for complete search history.

(56) References Cited

U.S. PATENT DOCUMENTS

| | | | |
|---|---|---|---|
| 4,501,734 A | 2/1985 | Tanaka et al. |
| 5,057,540 A | 10/1991 | Kensil et al. |
| 5,118,671 A | 6/1992 | Bombardelli et al. |
| 5,166,139 A | 11/1992 | Bombardelli et al. |
| 6,753,414 B2 | 6/2004 | Jin et al. |
| 2005/0004044 A1 | 1/2005 | Huang et al. |
| 2005/0175623 A1 | 8/2005 | Wang |

FOREIGN PATENT DOCUMENTS

| | | |
|---|---|---|
| CN | 1844138 | 10/2006 |
| CN | 1951394 | 4/2007 |
| CN | 101029070 | 9/2007 |
| CN | 101029072 | 9/2007 |
| CN | 101089008 | 12/2007 |
| PL | 191517 | 2/2000 |
| WO | WO 91/04052 | 4/1991 |
| WO | WO 96/03998 | 2/1996 |
| WO | WO 2004/091484 | 10/2004 |
| WO | WO 2005/082924 | 9/2005 |

OTHER PUBLICATIONS

Ma et al. Bioorganic & Medicinal Chemistry Letters 11 (2001) 2153-2156.*
Devendra et al. BMJ vol. 328, Mar. 27, 2004, pp. 750-754.*
PudMed Health, Autoimmune disorders, May 3, 2009, pp. 1-12.*
Merck Manual Professional, Dementia, Aug. 2007.*
Merck Manual Professional, Systemic Lupus Eerythematosus, Feb. 2008.*
Merck Manual Professional, Gout, Feb. 2013.*
Dangas et al. Circulation, 2002; 105: 2586-2587.*
Merck Manual Professional, Autosomal Dominant Polycystic Kidney Disease, Jul. 2009.*

* cited by examiner

*Primary Examiner* — Layla Bland
(74) *Attorney, Agent, or Firm* — Notaro, Michalos & Zaccaria P.C.

(57) ABSTRACT

This invention relates to novel saponin compounds of formula II wherein MBz denotes p-methoxybenzoyl, and R is selected from the group comprising $C_{6-10}$ aryl, $C_{6-10}$ aryl-$C_{1-4}$ alkyl-, $C_{1-18}$ alkanoyl, $C_{3-18}$ alkenyl, $C_{6-10}$ aryl-C(O)—, $C_{6-10}$ aryl-$C_{1-4}$ alkyl-C(O)—, wherein each of the groups can optionally be substituted. These compounds possess a selective cytostatic activity, useful, e.g., in the treatment of proliferative diseases. The invention further relates to methods of preparation of the novel compounds and to a pharmaceutical composition containing these compounds.

16 Claims, 6 Drawing Sheets

Formula II

SAPONIN COMPOUNDS, METHODS OF PREPARATION THEREOF, USE THEREOF AND PHARMACEUTICAL COMPOSITIONS

FIELD OF THE INVENTION

This invention relates to novel saponins, methods of their preparation and their use as medicaments, particularly in cancer treatment, as well as to pharmaceutical compositions.

BACKGROUND ART

Saponins form a large family of naturally occurring glycoconjugate compounds with considerable structural diversity. To the steroid, triterpenoid or steroidal alkaloid aglycone in these compounds a variable number of sugars is attached by the glycosidic bonds. The saponins display a broad spectrum of biological activities and practical applications. Their beneficial pharmaceutical activities have been applied inter alia as:

1) Absorption adjuvants in pharmaceutical compositions. For example, U.S. Pat. No. 4,501,734 describes the use of a triterpenoid saponin extract from *Sapindus mukurossi Gaertn.* to increase absorption of coadministered β-lactam antibiotic.
2) Immunological adjuvants in vaccine compositions against a variety of diseases. The saponins typically used as immunological adjuvants are triterpene glycosides extracted from the *Quillaja saponaria*, e.g., U.S. Pat. No. 5,057,540, WO 91/04052; similar application was described for the saponins Quinoa, pat. appl. WO 96/03998.
3) Anti-inflammatory, e.g., aescin, a saponin from *Aesculus hippocastanum* seeds; U.S. Pat. No. 5,118,671.
4) Anti-ulcerous agent, e.g., *Glyccyrrhiza glabra* saponins; U.S. Pat. No. 5,166,139.
5) Anti-cancer agents, e.g., a composition consisting of steroidal and triterpenoid saponins found in plants including *Quillaja saponaria Malina*, pat. appl. US 2005/0175623; OSW-1 saponin-patent CN 1951394, WO 2004/091484, US 2005/004044).

The saponin OSW-1, 3β16β17α-trihydroxycholest-5-en-22-one 16-O-{2-O-(4-methoxybenzoyl)-β-D-xylopyranosyl-(1→3)-2'-O-acetyl-α-L-arabinopyranoside (formula I) belongs to a family of cholestane glycosides, isolated from the bulbs of *Ornithogalum saundersiae* by Japanese scientists in 1992 (Kubo et al. Phytochemistry, 31, 3969, 1992).

Formula I

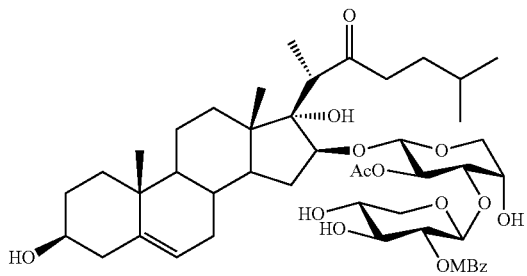

In NCI tests for leukemia HL-60 cancer cells the saponin OSW-1 exhibited cytotoxic activity in nanomolar concentrations, i.e. a cytotoxicity about 10-100 times higher than that of clinically applied anticancer agents, such as mitomycin C, adriamycin, cisplatin, camptothecin, and taxol. In the initial in vivo trials the saponin OSW-1 appears to prolong the life span of mice bearing P388 by 59% after only a single administration of 0.01 mg/kg. The effectiveness of OSW-1 in in vivo tests on mouse model of human cancer was demonstrated also by American researchers in the pat. appl. WO 2004/091484.

The saponin OSW-1 exhibits a unique mechanism of action. Its profile of cytotoxic activity does not match any of the six known mechanisms of action (alkylating agents, topoisomerase I inhibitors, topoisomerase II inhibitors, antimetabolites of RNA/DNA, antimetabolites of DNA, antimitotic agents). The first report concerning the OSW-1 mechanism of action was published in 2005. It was revealed that OSW-1 damaged the mitochondrial membrane and cristae in both human leukemia and pancreatic cancer cells, leading to the loss of transmembrane potential, increase of cytosolic calcium and activation of calcium-dependent apoptosis (Zhou et al., J. Natl. Cancer Inst. 97, 1781, 2005; Zhu et al., Mol. Pharmacol. 68, 1831, 2005).

So far several methods of OSW-1 synthesis have been described (patents: CN 101029070, CN 1844138, U.S. Pat. No. 6,753,414; publications: Deng et al., J. Org. Chem. 64, 202, 1999; Guo and Fuchs, Tetrahedron Lett. 39, 1099, 1998; Yu and Jin, Am. Chem. Soc. 123, 3369, 2001; ibid. 124, 6576, 2002; Morzycki and Wojtkielewicz, Carbohydr. Res. 337, 1269, 2002; Xu et al., Tetrahedron Lett. 44, 9375, 2003; Liu et al., Org. Chem. 73, 157, 2008; Tsubuki et al., Tetrahedron Lett. 49, 229, 2008). However, only two methods avoid the use of toxic and expensive $OsO_4$ in the crucial step of the OSW-1 aglycone synthesis. One of them was proposed by an American group in 2002 (U.S. Pat. No. 6,753,414). In the second method, elaborated by our group, the desired trans diol in ring D was obtained by the cleavage of the corresponding epoxide with $LiOH/H_2O_2$ (Morzycki et al., Tetrahedron 57, 2185, 2001; Morzycki and Wojtkielewicz, Carbohydr. Res. 337, 1269, 2002; patent PL 191517 B1).

A highly potent anticancer activity, selectivity towards malignant tumor cells and unique mechanism of action make the saponin OSW-1a promising novel anticancer agent. The application of this compound or its analogues as anticancer drugs was described in patents: CN 1951394, WO 2004/091484, US 2005/004044. Synthesis of OSW-1, because of its relatively complicated structure, consists of several steps and usually is not very efficient. Therefore, synthesis of analogues having a simplified structure, but retaining a high and selective activity was attempted. So far, a large number of OSW-1 analogues with modified aglycone or sugar was obtained and their cytostatic activity was tested (patents: CN 1010899008, CN 101029072, WO 2005/082924; publications: Guo et al., Bioorg. Med. Lett., 9, 419, 1999; Ma et al., Carbohydr. Res. 329, 495, 2000; Ma et al., Carbohydr. Res. 334, 159 2001; Ma et al., Bioorg. & Med. Chem. Lett. 11, 2153, 2001; Den et al., J. Chem. 22, 994, 2004; Morzycki et al., Bioorg. Med. Chem. Lett. 14, 3323, 2004; Deng et al., Bioorg. Med. Chem. Lett. 14, 2781, 2004; Matsuya et al., Eur. J. Org. Chem. 797, 2005; Shi et al., J. Org. Chem. 70, 10354, 2005; Tang et al., Bioorg.& Med. Chem. Lett. 17, 1003, 2007; Peng etr al., Bioorg.& Med. Chem. Lett. 17, 5506, 2007; Tschamber et al., Bioorg.& Med. Chem. Lett. 17, 5101, 2007; Wojtkielewicz et al., J. Med. Chem. 50, 3667, 2007).

A new series of derivatives of the saponin OSW-1 that are the object of the present invention are useful for selective inhibition of cell division cycle and induction of apoptosis in cancer cells. This group of new saponin derivatives is capable of selectively damaging the mitochondrial membrane and mitochondrial activity, thus allowing to achieve a very strong anticancer properties, particularly against leukaemia, pancreatic and melanoma cancers. Hence, they can be used as antimitotic and pro-apoptotic drugs, particularly as anticancer drugs. Furthermore, the new mechanism of action of the compounds provided by this invention promises their potential application as effective agents in the treatment of cancers resistant to conventional anticancer drugs.

DISCLOSURE OF THE INVENTION

The object of the present invention are novel saponin compounds of general formula II

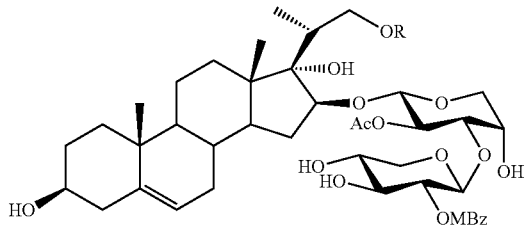

Formula II wherein

R is selected from the group comprising $C_{6-10}$ aryl-$C_{1-4}$ alkyl-, $C_{1-18}$ alkanoyl, $C_{3-18}$ alkenoyl, $C_{6-10}$ aryl-C(O)—, $C_{6-10}$ aryl-$C_{1-4}$ alkyl-C(O)—, wherein each of the groups can optionally be substituted by one or more, preferably by one to three, substituents selected from the group comprising $C_{1-6}$ alkyl, $C_{1-6}$ alkoxy, halogen, $C_{1-6}$ alkanoyl, $C_{1-6}$ alkenoyl, $C_{6-10}$ aryl-C(O)—, $C_{6-10}$ aryl, cyano, nitro and di($C_{1-6}$ alkyl) amino groups.

MBz denotes p-methoxybenzoyl.

Halogen is selected from the group comprising fluorine, bromine, chlorine and iodine atom.

Alkyl denotes a linear or branched hydrocarbyl chain containing the indicated number of carbon atoms and it can include an aliphatic cycle.

Alkoxy is a group —O-alkyl, wherein the alkyl is a linear or branched hydrocarbyl chain containing the indicated number of carbon atoms and it can include an aliphatic cycle.

Alkanoyl is a group alkyl-C(O)—, wherein the alkyl is a linear or branched hydrocarbyl chain containing the indicated number of carbon atoms and it can include an aliphatic cycle.

Alkenoyl is a group alkenyl-C(O)—, wherein the alkenyl is a linear or branched hydrocarbyl chain containing the indicated number of carbon atoms and at least one double bond and it can include an aliphatic cycle.

Aryl group has the indicated number of carbons and contains at least one aromatic ring. Preferably, the aryl is phenyl.

Arylalkyl group has the indicated number of carbons and contains at least one aromatic ring in the aryl moiety. Preferably, the $C_{6-10}$ aryl-$C_{1-4}$ alkyl is $C_{6-10}$ arylmethyl, more preferably, the $C_{6-10}$ aryl-$C_{1-4}$ alkyl is benzyl.

Preferably, the $C_{6-10}$ aryl-C(O)— is benzoyl.

Cyano denotes the group —CN.

Nitro denotes the group —$NO_2$.

Di($C_{1-6}$ alkyl)amino denotes a —$NZ_1Z_2$ group, wherein $Z_1$ and $Z_2$ represent $C_{1-6}$ alkyl groups and are the same or different.

It is to be understood that the present invention encompasses also the pharmaceutically acceptable salts and addition salts of the compounds of general formula II and in case there is an optically active atom in the structure, the invention encompasses all optically active isomers and mixtures thereof, including racemates.

Our studies have shown that the novel saponin OSW-1 analogues with modified side chain according to the present invention are highly cytostatic towards various malignant tumor cells. Thus, the object of the present invention is further the compounds of formula II for use as medicaments. More specifically, the object of the present invention is the compounds of formula II for use in the treatment of proliferative disorders.

The present invention further includes the use of the compounds of formula II in the preparation of a medicament destined for the treatment of proliferative disorders.

The proliferative disorders are disorders, which involve cell proliferation, such as cancer, restenosis, rheumatoid arthritis, lupus, type I diabetes, multiple sclerosis, Alzheimer's disease, growth of parasites (animal, protists), graft rejection (host versus graft disease), graft versus host disease, polycystic kidney disease, and gout. The cancers may include pancreatic cancers, leukemias, melanomas, breast cancers, prostate cancers, colon cancers, glioma cancers, and ovarian cancers. The cancers can be metastatic and/or drug resistant. Leukemias may include chronic lymphocytic leukemia (CLL), or acute myeloid leukemia. The pancreatic cancer may include a ductal adenocarcinoma, a mucinous cystadenocarcinoma, an acinar carcinoma, an unclassified large cell carcinoma, a small cell carcinoma, an intraductal papillary neoplasm, a mucinous cystadnoma, a papillary cystic neoplasm, or a pancreatoblastoma. The ovarian cancer may include carcinoma, a serous cell cancer, a mucinous cell cancer, an endometrioid cell cancer, a clear cell cancer, a mesonephroid cell cancer, a Brenner cell cancer, or a mixed epithelial cell cancer The present invention further encompasses a method of treatment of a mammal suffering from a proliferative disease, by administering a compound of formula II in a pharmaceutically effective amount to the mammal.

The novel saponins of the formula II can be used in combination with commonly used cytostatics, such as cyclophosphamid, 5-fluorouracil, adriamycin, mitoxantrone, mitomycin, camptothecin, cisplatin, methotrexate, taxol, or doxorubicin.

In another aspect, this invention includes the use of the novel compounds of the formula II for inhibiting cell proliferation and inducing apoptosis in cells.

In addition to the above described therapeutic applications, the compounds of the formula II can be used as a cell culture additive for in vitro controlling proliferative and/or apoptosis states of cells, for instance, by controlling the level of activation of mitochondrial damage.

The novel compounds of the present invention induce apoptosis in p53 mutated cancer cells. p53 is the mammal cell's own natural brake gene for stopping uncontrolled cell proliferation (cancer), thus being able to switch off the cancer. p53 as well as retinoblastoma (Rb) are two well characterised tumour suppressors whose inactivation may lead to uncontrolled cell proliferation and malignancy. Phosphorylation of these two proteins, which are involved in the cell cycle regulatory mechanisms, is known to modulate their function. Thus, potent p53 regulators represent a good tool for treatment of cancers due to regulation of wild/mutant type p53 protein in the selected cancers.

Studies carried out on the derivatives of the invention have demonstrated, in addition, a strong effect on the apoptosis of many cancer cell lines. It has been seen that apoptosis can be induced at stage $G_1$ or $G_2$ and following damage of the DNA, some cells stop at stage $G_1$ and p53-dependent apoptotic pathway is then induced. In other situations, it seems that cells stop at $G_2$/M stage in response to damage caused to the DNA, and activation of an independent p53 apoptotic path is observed. This path has proved particularly significant in the therapy of tumours in which a less active p53 is observed. The interest is therefore assessed that by application of the derivatives of the invention, p53-independent apoptosis will be stimulated in cells, which have stopped at stage $G_2$ through damage to the DNA using agents such as mitoxantrone or cis-platinum. The OSW1 derivatives of this invention can thus increase the therapeutic potential of the anti-tumour agents currently used.

The invention also includes a pharmaceutical composition, which comprises at least one compound of the formula II, or pharmaceutically acceptable salt or addition salt of a compound of general formula II, and a pharmaceutically acceptable carrier. The pharmaceutical composition may optionally further contain a cytostatic, preferably selected from the group comprising cyclophosphamid, 5-fluorouracil, adriamycin, mitoxantrone, mitomycin, camptothecin, cisplatin, methotrexate, taxol, and doxorubicin.

The novel compounds of this invention or their compositions can be administered systemically, regionally or locally, preferably by intravenous, intraartetial, intraperitoneal, intradermal, intratumoral, intramuscular, subcutaneous, oral, dermal, nasal, buccal, rectal, vaginal, inhalation, or topical administration.

The novel compounds of this invention can be used per se or as intermediates in the preparation of novel compounds having a wide variety of diagnostic, therapeutic and industrial utilities.

Pharmaceutical Compositions

The therapeutic composition comprise about 1% to about 95% of the active ingredient, single-dose forms of administration preferably comprising about 20% to about 90% of the active ingredient and administration forms, which are not single-dose preferably comprising about 5% to about 20% of the active ingredient. Unit dose forms may be, for example, coated tablets, tablets, ampoules, vials, suppositories or capsules. Other forms of administration are, for example, ointments, creams, pastes, foams, tinctures, lipsticks, drops, sprays, dispersions and the like. Examples are capsules containing from about 0.05 g to about 1.0 g of the active ingredient.

The pharmaceutical compositions of the present invention are prepared in a manner known per se, for example by means of conventional mixing, granulating, coating, dissolving or lyophilizing processes.

Preferably, solutions of the active ingredient, and in addition also suspensions or dispersions, especially isotonic aqueous solutions, dispersions or suspensions, are used, if being possible for these to be prepared before use, for example in the case of lyophilised compositions which comprise the active substance by itself or together with a carrier, for example mannitol. The pharmaceutical compositions can be sterilised and/or comprise excipients, for example preservatives, stabilisers, wetting agents and/or emulsifiers, solubilizing agents, salts for regulating the osmotic pressure and/or buffers, and they are prepared in a manner known per se, for example by means of conventional dissolving or lyophilising processes. The solutions or suspensions mentioned can comprise viscosity-increasing substances, such as sodium carboxymethylcellulose, dextran, polyvinylpyrrolidone or gelatine.

Suspensions in oil comprise, as the oily component, the vegetable, synthetic or semi-synthetic oils customary for injection purposes. Oils which may be mentioned are, in particular, liquid fatty acid esters which contain, as the acid component, a long-chain fatty acid having 8-22, in particular 12-22, carbon atoms, for example lauric acid, tridecylic acid, myristic acid, pentadecylic acid, palmitic acid, margaric acid, stearic acid, arachidonic acid, behenic acid or corresponding unsaturated acids, for example oleic acid, elaidic acid, euric acid, brasidic acid or linoleic acid, if appropriate with the addition of antioxidants, for example vitamin E, β-carotene or 3,5-di-tert-butyl-4-hydroxytoluene. The alcohol component of these fatty acid esters has not more than 6 carbon atoms and is mono- or polyhydric, for example mono-, di- or trihydric alcohol, for example methanol, ethanol, propanol, butanol, or pentanol, or isomers thereof, but in particular glycol and glycerol. Fatty acid esters are, for example: ethyl oleate, isopropyl myristate, isopropyl palmitate, "Labrafil M 2375" (polyoxyethylene glycerol trioleate from Gattefoseé, Paris), "Labrafil M 1944 CS" (unsaturated polyglycolated glycerides prepared by an alcoholysis of apricot kernel oil and made up of glycerides and polyethylene glycol esters; from Gattefoseé, Paris), "Labrasol" (saturated polyglycolated glycerides prepared by an alcoholysis of TCM and made up of glycerides and polyethylene glycol esters; from Gattefoseé, Paris) and/or "Miglyol 812" (triglyceride of saturated fatty acids of chain length $C_8$ to $C_{12}$ from Hüls AG, Germany), and in particular vegetable oils, such as cottonseed oil, almond oil, olive oil, castor oil, sesame oil, soybean oil and, in particular, groundnut oil.

The preparation of the injection compositions is carried out in the customary manner under sterile conditions, as are bottling, for example into ampoules or vials, and closing of the containers.

For example, pharmaceutical compositions for oral use can be obtained by combining the active ingredient with one or more solid carriers, if appropriate granulating the resulting mixture, and, if desired, processing the mixture or granules to tablets or coated tablet cores, if appropriate by addition of additional excipients.

Suitable carriers are, in particular, fillers, such as sugars, for example lactose, sucrose, mannitol or sorbitol, cellulose preparations and/or calcium phosphates, for example tricalcium diphosphate, or calcium hydrogen phosphate, and furthermore binders, such as starches, for example maize, wheat, rice or potato starch, methylcellulose, hydroxypropylmethylcellulose, sodium carboxymethylcellulose and/or polyvinylpyrrolidine, and/or, if desired, desintegrators, such as the above mentioned starches, and furthermore carboxymethylstarch, cross-linked polyvinylpyrrolidone, alginic acid or a salt thereof, such as sodium alginate. Additional excipients are, in particular, flow regulators and lubricants, for example salicylic acid, talc, stearic acid or salts thereof, such as magnesium stearate or calcium stearate, and/or polyethylene glycol, or derivatives thereof.

Coated tablet cores can be provided with suitable coatings which, if appropriate, are resistant to gastric juice, the coatings used being, inter alia, concentrated sugar solutions, which, if appropriate, comprise gum arabic, talc, polyvinylpyrrolidine, polyethylene glycol and/or titanium dioxide, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate. Dyes or pigments can be admixed to the tablets or coated tablet coatings, for example for identification or characterisation of different doses of active ingredient.

Pharmaceutical compositions, which can be used orally, are also hard capsules of gelatine and soft, closed capsules of gelatine and a plasticiser, such as glycerol or sorbitol. The hard capsules can contain the active ingredient in the form of granules, mixed for example with fillers, such as maize starch, binders and/or lubricants, such as talc or magnesium stearate, and stabilisers if appropriate. In soft capsules, the active ingredient is preferably dissolved or suspended in suitable liquid excipients, such as greasy oils, paraffin oil or liquid polyethylene glycol or fatty acid esters of ethylene glycol or propylene glycol, it being likewise possible to add stabilisers and detergents, for example of the polyethylene sorbitan fatty acid ester type.

Other oral forms of administration are, for example, syrups prepared in the customary manner, which comprise the active ingredient, for example, in suspended form and in a concentration of about 5% to 20%, preferably about 10% or in a similar concentration which results in a suitable individual dose, for example, when 5 or 10 ml are measured out. Other forms are, for example, also pulverulent or liquid concentrates for preparing of shakes, for example in milk. Such concentrates can also be packed in unit dose quantities.

Pharmaceutical compositions, which can be used rectally, are, for example, suppositories that comprise a combination of the active ingredient with a suppository base. Suitable suppository bases are, for example, naturally occurring or synthetic triglycerides, paraffin hydrocarbons, polyethylene glycols or higher alkanols.

Compositions which are suitable for parental administration are aqueous solutions of an active ingredient in water-soluble form, for example of water-soluble salt, or aqueous injection suspensions, which comprise viscosity-increasing substances, for example sodium carboxymethylcellulose, sorbitol and/or dextran, and, if appropriate, stabilizers. The active ingredient can also be present here in the form of a lyophilisate, if appropriate, together with excipients, and be dissolved before parenteral administration by addition of suitable solvents. Solutions such as are used, for example, for parental administration can also be used as infusion solutions. Preferred preservatives are, for example, antioxidants, such as ascorbic acid, or microbicides, such as sorbic or benzoic acid.

Ointments are oil-in-water emulsions which comprise not more than 70%, preferably 20-50% of water or aqueous phase. The fatty phase consists, in particular, hydrocarbons, for example vaseline, paraffin oil or hard paraffins, which preferably comprise suitable hydroxy compounds, such as fatty alcohols or esters thereof, for example cetyl alcohol, or wool wax alcohols, such as wool wax, to improve the water-binding capacity. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example glycerol, propylene glycol, sorbitol and/or polyethylene glycol, or preservatives and odoriferous substances.

Tinctures and solutions usually comprise an aqueous-ethanolic base to which, humectants for reducing evaporation, such as polyalcohols, for example glycerol, glycols and/or polyethylene glycol, and re-oiling substances, such as fatty acid esters with lower polyethylene glycols, i.e. lipophilic substances soluble in the aqueous mixture to substitute the fatty substances removed from the skin with ethanol, and, if necessary, other excipients and additives, are admixed.

The invention also relates to a process or method for treatment of the disease states mentioned above. The compounds can be administered prophylactically or therapeutically as such or in the form of pharmaceutical compositions, preferably in an amount, which is effective against the diseases mentioned. With a warm-blooded animal, for example a human, requiring such treatment, the compounds are used, in particular, in the form of pharmaceutical composition. A daily dose of about 0.1 to about 5 g, preferably 0.5 g to about 2 g, of a compound of the present invention is administered here for a body weight of about 70 kg.

Methods of Preparation

The saponin compounds of formula II may be prepared from (20R)-20-methyl-6β-methoxy-3α,5α-cyclopregnane-16β,17α,21-triol of formula III.

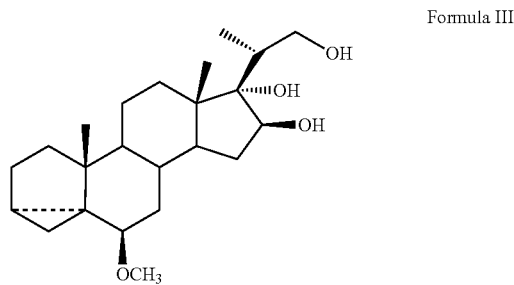

Formula III

The method of preparing compounds of formula II, which is especially suitable for the preparation of compounds of formula II, wherein R is arylalkyl or substituted arylalkyl, comprises the following steps:
a) Williamson etherification of the primary 22-hydroxyl group of the steroidal triol of formula III with a corresponding arylalkyl halide, or substituted arylalkyl halide in the presence of a base (e.g., sodium hydride, potassium tert-butoxide) in an etheric solvent (e.g., THF, diethyl ether, dioxane);
b) glycosylation of the steroidal aglycone obtained as described in step (a) with a disaccharide donor of formula IV

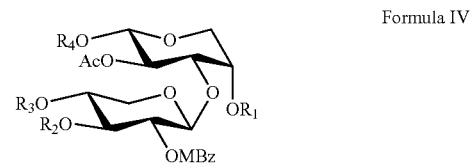

Formula IV wherein $R_1$, $R_2$, $R_3$ are protective groups for alcohols (e.g., triethylsilyl) and $OR_4$ is a leaving group [e.g., —O—C(=NH)—CCl$_3$];
c) removal of the protective groups from the obtained glycoside with an acidic catalyst (e.g., p-toluenesulfonic acid).

The method of preparation of compounds of formula II, which is especially suitable for the preparation of compounds of formula II, wherein R is $C_{1-18}$ alkanoyl, $C_{3-18}$ alkenyl, —C(O)aryl or —C(O)alkylaryl, all of them optionally substituted, can be obtained by a process comprising the following steps:
a) selective protection of the primary 22-hydroxyl group of steroidal triol of formula III (e.g., as benzyl ether, triethylsilyl ether);
b) glycosylation of the steroidal aglycone obtained as described in step (a) with a glycosyl donor of formula IV wherein $R_1$, $R_2$, $R_3$ are protective groups for alcohols (e.g., triethylsilyl) and $OR_4$ is a leaving group [e.g. —O—C(=NH)—CCl$_3$];

c) selective deprotection of the primary 22-hydroxyl group of the obtained glycoside;
d) esterification of primary alcohol with a corresponding carboxylic acid or a carboxylic acid derivative (e.g., halide, anhydride);
e) removal of the protective groups from the obtained glycoside using an acidic catalyst (e.g., p-toluenesulfonic acid).

EXAMPLES OF CARRYING OUT THE INVENTION

Figure 1:
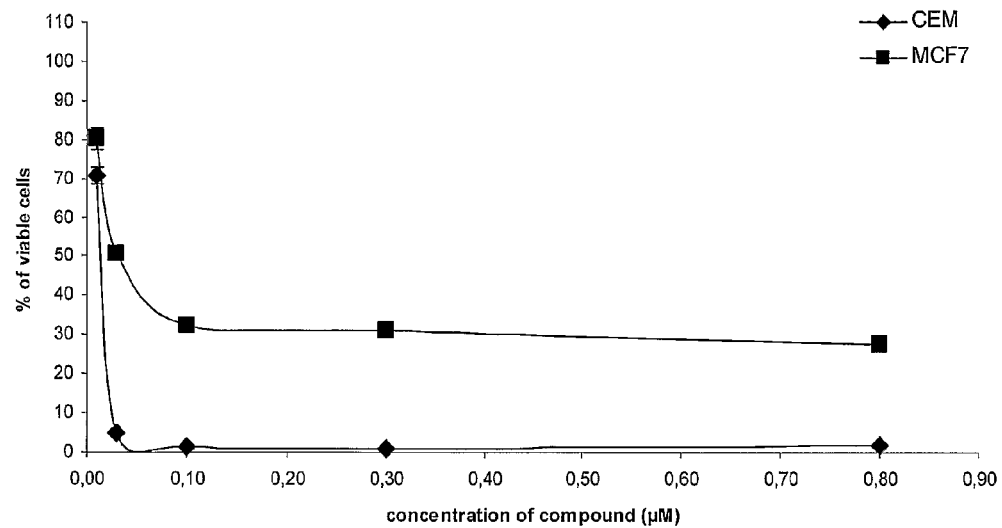
FIG. 1: The dose-dependent antiproliferative activity of compounds 9 and 10 against human breast cancer cell line MCF7 and CEM leukemia cancer cell line. The cells were treated for 72 h with increasing concentrations of the compounds and then the number of viable cells was determined by a Calcein AM assay. Results represent the average±SD for three independent experiments. Compounds 9 and 10 significantly reduce the number of living cells.
Figure 1:
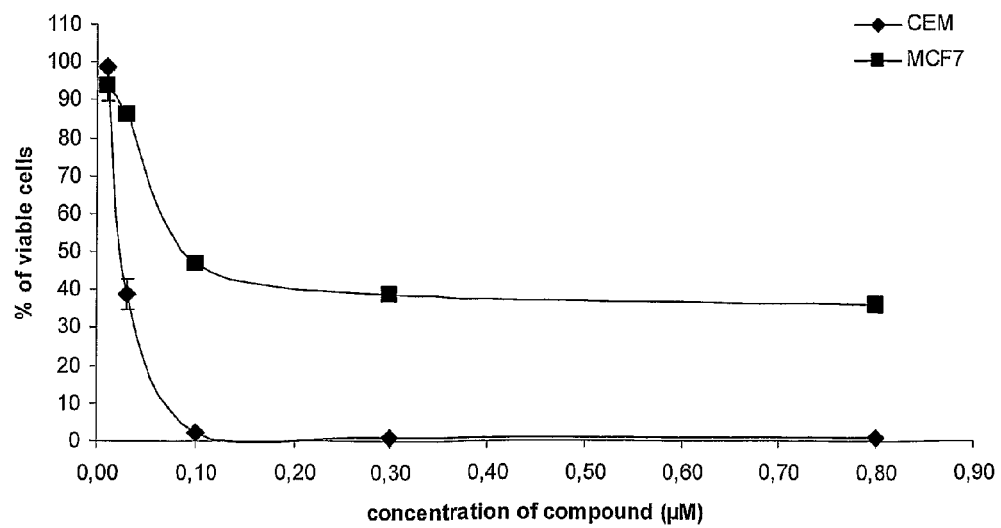

The invention is further illustrated by the following examples, which should not be construed as further limiting.
Methods:
Analytic Methods:

NMR spectra were recorded in CDCl$_3$ solutions with a Bruker Avance II 400 MHz spectrometer using the residual solvent as internal standard (only selected signals in the $^1$H-NMR spectra are reported). Infrared spectra were recorded on a Nicolet series II Magna-IR 550 FT-IR spectrometer in anhydrous chloroform solutions. Mass spectra were obtained at 70 eV with an AMD-604 spectrometer.

The reaction products were isolated by column chromatography performed on 70-230 mesh silica gel (J. T. Baker).

Abbreviations used: Ac—acetyl; DCC—dicyclohexylcarbodiimide; DMAP—4-N,N-dimethylaminopyridine; DMSO—dimethyl sulfoxide; MBz—p-methoxybenzoyl; pGI$_{50}$—negative log of the molar concentration causing 50% growth inhibition of tumor cells; OD—optical density; p-TsOH—p-toluenesulfonic acid; TES—triethylsilyl; THF—tetrahydrofuran; TMS—trimethylsilyl; Tf—trifluoromethanesulfonate.

Cell Culture:

Stock solutions (10 mmol/l) of the tested compounds were prepared by dissolving relevant quantity of the substance in DMSO. Dulbecco's modified Eagle's medium (DMEM, RPMI 1640, F-12 medium), fetal bovine serum (FBS), L-glutamine, penicillin, streptomycin were purchased from Sigma (MO, USA). Calcein AM was obtained from Molecular Probes (Invitrogen Corporation, CA, USA).

The screening cell lines (T-lymphoblastic leukaemia cell line CEM, breast carcinoma cell line MCF-7, cervical carcinoma cell line HeLa, human glioblastoma cell line T98, human malignant melanoma G-361, human osteogenic sarcoma cell line HOS, carcinomic human alveolar basal epithelial cells A549, human colon carcinoma cells HCT 116 and human fibroblasts BJ) were obtained from the American Type Culture Collection (Manassas, Va., USA). All cell lines were cultured in DMEM medium (Sigma, Mo., USA). Medium was supplemented with 10% heat-inactivated fetal bovine serum, 2 mmol/l L-glutamine and 1% penicillin-streptomycin. The cell lines were maintained under standard cell culture conditions at 37° C. and 5% $CO_2$ in a humid environment. Cells were subcultured twice or three times a week using the standard trypsinization procedure.

Statistical Analysis:

All experiments were performed in triplicates at least in three independent experiments. All quantitative data are presented as mean±standard error (SEM) or as mean±standard deviation (SD).

Example 1

Synthesis of (20S)-21-benzyloxy-20-methylpregn-5-ene-3β,16β17α-triol 16-O-{2-O-(4-methoxybenzoyl)-β-D-xylopyranosyl-(1→3)-2'-O-acetyl-α-L-arabinopyranoside (formula II, R=benzyl; compound 1)

Regioselective benzylation of (20S)-6β-methoxy-20-methyl-3α,5α-cyclopregnane-16β,17α,21-triol To the solution of (20S)-6β-methoxy-20-methyl-3α,5α-cyclopregnane-16β,17α,21-triol (0.5 g, 1.3 mmol, patent PL 191517 B1) in dry THF (15 ml), NaH (1.5 eq, 0.048 g) was added at 0° C. The reaction mixture Was stirred 15 min at 0° C., then solution of benzyl bromide (1.1 eq, 0.17 ml) in THF (2 ml) was added dropwise. The reaction mixture was stirred 1 h at reflux. The reaction was carefully quenched with water and extracted with ether. The extract was dried over MgSO$_4$ and solvent was evaporated in vacuo. The crude product was purified by silica gel column chromatography with hexane-ethyl acetate (8:2, v/v).

(20S)-21-Benzyloxy-6β-methoxy-20-methyl-3α,5α-cyclopregnane-16β,17α-diol (0.43 g, 70%)

IR(CHCl$_3$) ν=3606, 3440, 1455, 1091 cm$^{-1}$; $^1$H NMR (400 MHz, CDCl$_3$, 25° C., TMS), δ=7.34 (m, 5H), 4.54 (s, 2H), 3.92 (bs, 1H), 3.90 (m, 1H), 3.70 (t, J=9.0, 1H), 3.43 (dd, J$_1$=3.2, J$_2$=9.2, 1H), 3.33 (s, 3H), 2.78 (m, 1H), 1.04 (s, 3H), 1.01 (s, 3H), 0.95 (d, J=7.1, 3H), 0.66 (m 1H), 0.44 (dd, J$_1$=5.1, J$_2$=8.0, 1H); $^{13}$C NMR (100 MHz, CDCl$_3$, 25° C., TMS), δ=137.3 (C), 128.6 (2CH), 127.9 (CH), 127.8 (2CH), 85.6 (C), 82.3 (CH), 80.9 (CH), 74.0 (CH$_2$), 73.7 (CH$_2$), 56.5 (CH$_3$), 48.4 (CH), 47.6 (CH), 47.4 (C), 43.3 (C), 35.4 (C), 34.7 (CH$_2$), 34.6 (CH), 34.5 (CH$_2$), 33.37 (CH$_2$), 33.36

($CH_2$), 30.4 (CH), 25.0 ($CH_2$), 22.2 ($CH_2$), 21.6 (CH), 19.3 ($CH_3$), 13.4 ($CH_3$), 13.0 ($CH_2$), 12.9 ($CH_3$);

Glycosylation with 2-O-(4-methoxybenzoyl)-3,4-di-O-triethylsilyl-β-D-xylopyranosyl-(1→3)-2'-O-acetyl-4'-O-triethylosilyl-α-L-arabinopyranosyl trichloroacetimidate A solution of (20S)-21-benzyloxy-6β-methoxy-20-methyl-3α,5α-cyclopregnane-16β17α-diol (0.19 g, 0.41 mmol) and 2-O-(4-methoxybenzoyl)-3,4-di-O-triethylsilyl-β-D-xylopyranosyl-(1→3)-2'-O-acetyl-4'-O-triethylsilyl-α-L-arabinopyranosyl trichloroacetimidate (1.2 eq, 0.46 g, S. Deng, B. Yu, Y. Lou, Y. Hui, J. Org. Chem. 64, 202 (1999)) in dry dichloromethane (10 ml) was stirred with molecular sieves 4 Å MS (1.28 g) for 15 min at room temperature, then the reaction mixture was cooled to −68° C. (dry ice—ethanol bath) and 0.14 M solution of TMSOTf in dry dichloromethane (1.1 ml) was slowly added. The reaction mixture was stirred for additional 30 min at −40° C. (dry ice—acetonitrile bath), quenched with triehylamine (0.5 ml), then molecular sieves were filtered off and the solvent was evaporated in vacuo. The crude product was purified by silica gel column chromatography with hexane-ethyl acetate (95:5, v/v).

(20S)-21-Benzyloxy-6β-methoxy-20-methyl-3α,5α-cyclopregnane-16β17α-diol 16-0-{2-O-(4-methoxybenzoyl)-3,4-di-O-triethylsilyl-β-D-xylopyranosyl-(1→3)-2'-O-acetyl-4'-O-triethylsilyl-α-L-arabinopyranoside} (0.34 g, 66%)

IR($CHCl_3$) ν=3517, 3446, 3405, 1729, 1607, 1511 1458, 1096, 909, 615 $cm^{-1}$; $^1H$ NMR (400 MHz, $CDCl_3$, 25° C., TMS), δ=7.98 (d, J=9.0, 2H), 7.32 (m, 5H), 6.91 (d, J=9.0, 2H), 4.90 (m, 2H), 4.72 (d, J=5.3, 1H), 4.57 (d, J=12.0, 1H), 4.37 (d, J=12.0, 1H), 4.18 (s, 1H), 4.15 (m, 1H), 3.99 (m, 1H), 3.87 (s,3H), 3.87-3.59 (m, 6H), 3.47 (dd, $J_1$=4.0, $J_2$=7.8, 1H), 3.32-3.25 (m, 3H), 3.30 (s 3H), 2.74 (m 1H), 1.85 (s, 3H), 1.10 (d, J=7.2, 3H), 1.01-0.87 (m, 34H), 0.67-0.54 (m 19H), 0.40 (dd, $J_1$=5.1, $J_2$=8.0, 1H); $^{13}C$ NMR (100 MHz, $CDCl_3$, 25° C., TMS), δ=168.7 (C), 164.6 (C), 163.3 (C), 137.9 (C), 131.8 (2CH), 128.4 (3CH), 128.1 (3CH), 127.8 (CH), 122.7 (C), 113.2 (2CH), 102.5 (CH), 100.7 (CH), 90.6 (CH), 87.3 (C), 82.4 (CH), 75.9 ($CH_2$), 73.7 (2$CH_2$), 73.5 (CH), 71.0 (CH), 70.8 (CH), 68.7 (CH), 64.6 ($CH_2$), 56.4 ($CH_3$), 55.4 ($CH_3$), 48.0 (CH), 47.5 (CH), 46.6 (C), 43.3 (C), 35.5 (C), 35.0 ($CH_2$), 34.5 ($CH_2$), 33.9 (CH), 33.3 ($CH_2$), 32.9 ($CH_2$), 30.3 (CH), 25.0 ($CH_2$), 22.3 ($CH_2$), 21.7 (CH), 20.8 ($CH_3$), 19.2 ($CH_3$), 13.7 ($CH_3$), 13.5 ($CH_3$), 12.9 ($CH_2$), 6.9 (3$CH_3$), 6.83 (3$CH_3$), 6.80 (3$CH_3$), 5.03 (3$CH_2$), 5.00 (3$CH_2$), 4.9 (3$CH_2$) ppm.

The Removal of Protective Groups from the Glycoside

To the solution of the glycoside (0.018 g, 0.014 mmol) in dioxane—water (7:1, v/v; 3.2 ml) mixture, p-TsOHx$H_2O$ (0.002 g) was added. The reaction mixture was stirred for 1.5 hour at 75° C. Then the reaction mixture was poured into the water and product was extracted with ethyl acetate, the extract was dried over $MgSO_4$ and the solvent was evaporated in vacuum. The saponin (0.015 g, 93%) was purified by silica gel column chromatography (elution with dichloromethane-methanol; 97:3, v/v).

(20R)-21-Benzyloxy-20-methylpregn-5-ene-3β,16β,17α-triol 16-O-{2-O-(4-methoxybenzoyl)-β-D-xylopyranosyl-(1→3)-2'-O-acetyl-α-L-arabinopyranoside} (compound 1)

IR($CHCl_3$) ν=3434, 1738, 1722, 1606, 1512, 1454, 1068, 845 $cm^{-1}$; $^1H$ NMR (400 MHz, $CDCl_3$, 25° C., TMS), δ=8.02 (d, J=8.7, 2H), 7.28 (m 5H), 6.96 (d, J=8.7, 2H), 5.31 (1H) 4.90 (dd, $J_1$=4.9, $J_2$=6.7, 1H), 4.84 (dd, J=6.8, $J_2$=7.3, 1H), 4.70 (d, J=6.5, 1H), 4.51 (d, J=12.0, 1H), 4.19 (d, J=12.0, 1H), 4.16 (dd, $J_1$=4.5, $J_2$=11.6, 1H), 4.02 (s, 1H), 3.94 (m, 1H), 3.88 (s, 3H), 3.87 (m, 3H), 3.72 (m, 2H), 3.52 (m, 4H), 3.45-3.38 (m, 4H), 2.85 (m, 1H), 1.81 (s, 3H), 1.01 (s, 3H), 0.99 (d, J=9.0, 3H), 0.77 (s, 3H) ppm; $^{13}C$ NMR (100 MHz, $CDCl_3$, 25° C., TMS), δ=169.3 (C), 166.3 (C), 164.1 (C), 140.6 (C), 137.6 (CH), 132.2 (2CH), 128.4 (2CH), 128.2 (2CH), 127.9 (CH), 121.6 (CH), 121.3 (C), 113.9 (2CH), 101.9 (CH), 101.8 (CH), 90.5 (CH), 87.2 (C), 80.4 (CH), 75.4 ($CH_2$), 74.5 (CH), 74.0 ($CH_2$), 73.6 (CH), 71.8 (CH), 70.7 (CH), 69.7 (CH), 66.4 (CH), 64.6 ($CH_2$), 63.3 ($CH_2$), 55.5 ($CH_3$), 49.7 (CH), 48.3 (CH), 46.2 (C), 42.3 ($CH_2$, C), 37.2 ($CH_2$), 36.4 (C), 35.1 ($CH_2$), 33.8 (CH), 32.4 ($CH_2$), 31.9 (CH), 31.6 ($CH_2$), 29.7 ($CH_2$), 20.6 ($CH_2$, $CH_3$), 19.4 ($CH_3$), 13.7 ($CH_3$), 12.9 ($CH_3$) ppm. ESI-MS m/z (%) 917.4 ($MNa^+$).

Example 2

Synthesis of (20R)-21-O-benzoyl-20-methylpregn-5-ene-3β,16β,17α,21-tetraol 16-O-{2-O-(4-methoxybenzoyl)-β-D-xylopyranosyl-(1→3)-2'-O-acetyl-α-L-arabinopyranoside} (formula II, R=benzoyl; compound 2)

The removal of a benzyl group in (20R)-21-benzyloxy-6β-methoxy-20-methyl-3α,5α-cyclopregnane-16β,17α-diol 16-O-{2-O-(4-methoxybenzoyl)-3,4-di-O-triethylsilyl-β-D-xylopyranosyl-(1→3)-2'-O-acetyl-4'-O-triethylsilyl-α-L-arabinopyranoside}

To the stirred solution of glycoside (0.5 g, 0.4 mmol) in ethyl acetate and anhydrous ethanol (1:1 v/v; 20 ml), 10% Pd/C (0.53 g) and triethylamine (0.18 ml) was added. The reaction was carried out under hydrogen atmosphere (5 MPa) at 50° C. for 20 h. Then the catalyst was filtered off and the solvent was evaporated in vacuo. The desired alcohol (0.38 g, 82%) was purified by silica gel column chromatography with hexane-ethyl acetate (8:2, v/v) elution.

(20R)-6β-Methoxy-20-methyl-3α,5α-cyclopregnane-16β,17α,21-triol 16-O-{2-O-(4-methoxybenzoyl)-3,4-di-O-triethylsilyl-β-D-xylopyranosyl-(1→3)-2'-O-acetyl-4'-O-triethylsilyl-α-L-arabinopyranoside} (0.38 g, 82%)

IR($CHCl_3$) ν=3688, 3486, 1725, 1607, 1511, 1458, 1255, 1096 $cm^{-1}$; $^1H$ NMR (400 MHz, $CDCl_3$, 25° C., TMS), δ=7.99 (d, J=9.0, 2H), 6.91 (d, J=9.0, 2H), 4.96 (dd, $J_1$=4.9, $J_2$=7.1, 1H), 4.91 (dd, $J_1$=5.5, $J_2$=6.9, 1H), 4.39 (d, J=5.3, 1H), 4.36 (d, J=4.9, 1H), 4.14 (m, 1H), 4.01 (m, 1H), 3.87 (s, 3H), 3.68-3.78 (m, 6H), 3.54 (dd, $J_1$=3.1, $J_2$=11.0, 1H), 3.36 (m, 1H), 3.32 (s, 3H), 3.24 (dd, $J_1$=7.7, $J_2$=11.4, 1H), 2.76 (m, 1H), 1.90 (s, 3H), 0.86-1.07 (m, 34H), 0.53-0.66 (m, 19H), 0.42 (dd, 5.1, $J_2$=7.9, 1H) ppm; $^{13}C$ NMR (100 MHz, $CDCl_3$, 25° C., TMS), δ=169.1 (C), 164.8 (C), 163.3 (C), 131.9 (2CH), 122.6 (C), 113.4 (2CH), 102.3 (CH), 101.1 (CH), 89.5 (CH), 88.1 (C), 82.3 (2CH), 74.2 (CH), 71.3, (CH), 70.8 (CH), 67.7 (2$CH_2$), 64.7 ($CH_2$), 56.4 ($CH_3$), 55.4 ($CH_3$), 48.0 (2CH), 47.5 (2CH), 47.0 (C), 43.4 (C), 35.5 (C), 35.4 (CH), 34.71 ($CH_2$), 34.67 ($CH_2$), 33.3 ($CH_2$), 32.9 ($CH_2$), 30.3 (CH), 25.0 ($CH_2$), 22.2 ($CH_2$), 21.6 (CH), 20.8 ($CH_3$), 19.2 ($CH_3$), 13.6 ($CH_2$), 13.0 ($CH_3$), 12.4 ($CH_3$), 6.9 (3$CH_3$), 6.83 (3$CH_3$), 6.81 (3$CH_3$), 5.1 (3$CH_2$), 5.0 (3$CH_2$), 4.8 (3$CH_2$) ppm.

Esterification with Benzoic Acid

The solution of (20R)-6β-methoxy-20-methyl-3α,5α-cyclopregnane-16β,17α,21-triol 16-O-{2-O-(4-methoxybenzoyl)-3,4-di-O-triethylsilyl-β-D-xylopyranosyl-(1→3)-2'-O-acetyl-4'-O-triethylosilyl-α-L-arabinopyranoside} (0.049 g, 0.042 mmol), benzoic acid (0.006 g 0.049 mmol), DCC (0.01 g, 0.049 mmol), and DMAP (0.5 mg, 0.004 mmol) in dichloromethane (5 ml) was stirred for 16 h at room temperature. Then N,N-dicyclohexyl urea was filtered off and the filtrate was washed with 5% acetic acid, water, dried over $MgSO_4$ and the solvent was evaporated. Silica gel column chromatography (elution with hexane-ethyl acetate; 85:15, v/v) afforded the ester, which was subsequently subjected to deprotection of functional groups.

(20R)-21-O-Benzoyl-6β-methoxy-20-methyl-3α,5α-cyclopregnane-16β,17α,21-triol 16-O-{2-O-(4-methoxybenzoyl)-3,4-di-O-triethylsilyl-β-D-xylopyranosyl-(1-43)-2'-O-acetyl-4'-O-triethylsilyl-α-L-arabinopyranoside} [0.047 g, 89%; $^1$H NMR (400 MHz, $CDCl_3$, 25° C., TMS), δ=7.96 (m, 4H), 7.52 (m, 1H), 7.43 (m, 2H), 6.85 (d, J=9.0, 2H), 5.06 (dd, $J_1$=5.6, $J_2$=8.1, 1H), 4.94 (m, 1H), 4.71 (d, J=5.5, 1H), 4.36 (m, 2H), 4.01-4.08 (m, 5H), 3.85 (s, 4H), 3.40-3.71 (m, 6H), 3.31 (s, 3H), 3.24 (m, 1H), 2.75 (m, 1H), 1.83 (s, 3H), 0.88-1.26 (m, 34H), 0.42-0.65 (m, 20H) ppm.

The Removal of Protective Groups from the Glycoside

To the solution of the glycoside (0.047 g, 0.037 mmol) in dioxane:water (7:1, v/v; 3.2 ml) mixture, p-TsOHxH$_2$O (0.002 g) was added. The reaction mixture was stirred for 1.5 hour at 75° C. Then the reaction mixture was poured into the water and product was extracted with ethyl acetate, the extract was dried over $MgSO_4$ and the solvent was evaporated in vacuo. The saponin (0.03 g, 88%) was purified by silica gel column chromatography (elution with dichloromethane-methanol; 97:3, v/v).

(20R)-21-O-Benzoyl-20-methylpregn-5-ene-3β,16β,17α,21-tetraol 16-O-{2-O-(4-methoxybenzoyl)-β-D-xylopyranosylo-(1→3)-2'-O-acetyl-α-L-arabinopyranoside} (compound 2)

IR (KBr) ν=3448, 1717, 1605, 1512, 1459, 1259, 1049 cm$^{-1}$; 1H NMR (400 MHz, $CDCl_3$/MeOD, 25° C., TMS), δ=7.80 (m, 4H), 7.45 (t, J=7.4, 1H), 7.31 (m, 2H), 6.73 (d, J=8.8, 2H), 5.18 (m, 1H), 4.94 (dd, 7.3, $J_2$=9.2, 1H), 1H), 4.76 (t, 1H), 4.44 (d, J=7.0, 1H) 4.23 (d, J=7.2, 1H) 4.14 (m, 1H), 4.06 (m, 1H), 3.85 (m, 2H), 3.73 (s, 1H), 3.71 (s, 3H), 3.44-3.59 (m, 5H), 3.35 (m, 2H), 3.17 (m, 1H), 1.67 (s, 3H), 0.94 (d, J=6.9, 3H), 0.87 (s, 3H), 0.71 (s, 3H), ppm; $^{13}$C NMR (100 MHz, $CDCl_3$, 25° C., TMS), δ=169.4 (C), 166.6 (C), 166.1 (C), 164.0 (C), 140.6 (C), 133.0 (CH), 132.1 (2CH), 130.1 (C), 129.4 (2CH), 128.5 (2CH), 121.5 (CH), 121.2 (C), 113.9 (2CH), 101.9 (CH), 101.3 (CH), 88.5 (CH), 86.9 (C), 79.7 (CH), 74.3 (CH), 73.5 (CH), 71.7 (CH), 70.5 (CH), 69.7 (CH), 68.8 ($CH_2$), 66.7 (CH), 64.3 ($CH_2$), 63.7 ($CH_2$), 55.5 ($CH_3$), 53.4 ($CH_2$), 49.7 (CH), 48.5 (CH), 46.7 (C), 42.3 ($CH_2$), 37.2 ($CH_2$), 36.4 (C), 34.1 (CH), 32.5 ($CH_2$), 31.8 (CH), 31.7 ($CH_2$), 31.6 ($CH_2$), 29.7 ($CH_2$), 20.6 ($CH_2$), 19.4 ($CH_3$), 13.0 ($CH_3$), 12.2 ($CH_3$) ppm; ESI-MS m/z (%) 931.4 (MNa$^+$); for $C_{49}H_{64}O_{16}Na$, calculated: 931.40866. found: 931.40631.

Example 3

Synthesis of (20R)-21-O-(4-methoxybenzoyl)-20-methylopregn-5-ene-3β,16β,17α,21-tetraol 16-O-{2-O-(4-methoxybenzoyl)-β-D-xylopyranosyl-(1→3)-2'-O-acetyl-α-L-arabinopyranoside (formula II, R=4-methoxybenzoyl; compound 3)

Esterification with 4-Methoxybenzoic Acid

Esterification of (20R)-6β-methoxy-20-methyl-3α,5α-cyclopregnane-16β,17α,21-triol 16-O-{2-O-(4-methoxybenzoyl)-3,4-di-O-triethylsilyl-β-D-xylopyranosyl-(1→3)-2'-O-acetyl-4'-O-triethylsilyl-α-L-arabinopyranoside} with 4-methoxybenzoic acid was carried out similarly as in example 2. Silica gel column chromatography with hexane-ethyl acetate; 84:16, v/v) elution of forded the desired ester in 65% yield, which was subsequently subjected to deprotection of the functional groups.

(20R)-21-O-(4-Methoxybenzoyl)-6β-methoxy-20-methyl-3α,5α-cyclopregnane-16β,17α,21-triol 16-O-{2-O-(4-methoxybenzoyl)-3,4-di-O-triethylsilyl-β-D-xylopyranosyl-(1→3)-2'-O-acetyl-4'-O-triethylsilyl-α-L-arabinopyranoside}

$^1$H NMR (400 MHz, $CDCl_3$, 25° C., TMS), δ=8.07 (d, J=8.8, 2H), 7.95 (d, J=8.8, 2H), 6.96 (d, J=8.8, 2H), 6.86 (d, J=8.8, 2H), 5.06 (m, 1H), 4.95 (t, J=6.1, 1H), 4.74 (m, 1H), 4.36 (m, 2H), 4.25 (dd, $J_1$=3.4, $J_2$=11.1, 1H), 4.12 (m, 1H), 4.01 (m, 1H), 3.89 (s, 3H), 3.85 (s, 4H), 3.60-3.75 (m, 4H), 3.37 (m, 1H), 3.31 (s, 3H), 3.24 (m, 1H), 2.75 (m, 1H), 1.85 (s, 3H), 0.86-1.27 (m, 34H), 0.53-0.66 (m, 19H), 0.42 (m, 1H) ppm.

The Removal of Protective Groups from the Glycoside

The ester obtained in the previous step was treated with p-toluenesulfonic acid, according to the procedure described in example 2. The purification of the crude product by silica gel column chromatography (elution with dichloromethane—methanol; 94:6, v/v) afforded the desired saponin in 90% yield.

(20R)-21-O-(4-Methoxybenzoyl)-20-methylopregn-5-ene-3β,16β,17α,21-tetraol 16-O-{2-O-(4-methoxybenzoyl)-β-D-xylopyranosyl-O-acetyl-α-L-arabinopyranoside} (compound 3)

IR(CHCl$_3$) ν=3588, 3384, 1738, 1724, 1715, 1607, 1512, 1259, 1196 cm$^{-1}$; $^1$H NMR (400 MHz, $CDCl_3$/MeOD, 25° C., TMS), δ=7.91 (d, J=8.8, 2H), 7.87 (d, J=8.8, 2H), 6.88 (d, J=8.9, 2H), 6.85 (d, J=8.9, 2H), 5.30 (m, 1H), 5.06 (dd, $J_1$=6.7, $J_2$=8.4, 1H), 4.89 (J=7.0, $J_2$=7.6, 1H), 4.63 (d, J=6.5, 1H), 4.35 (d, J=6.6, 1H), 4.26 (m, 1H), 4.11 (dd, J=3.5, $J_2$=11.0, 1H), 4.05 (dd, J=4.5, $J_2$=11.7, 1H), 3.95 (m, 2H), 3.84 (s, 3H), 3.82 (s, 3H), 3.61-3.71 (m, 4H), 3.45 (m, 2H), 3.34 (dd, $J_1$=8.6, $J_2$=11.6, 1H), 1.64 (s, 3H), 1.01 (d, J=7.0, 3H), 0.98 (s, 3H), 0.83 (s, 3H) ppm; $^{13}$C NMR (100 MHz, $CDCl_3$/MeOD, 25° C., TMS), δ=169.5 (C), 166.6 (C), 165.7 (C), 163.8 (C), 163.5 (C), 140.6 (C), 131.9 (2CH), 131.4 (2CH), 122.4 (C), 121.6 (C), 121.5 (CH), 113.71 (2CH), 113.69 (2CH), 102.4 (CH), 101.7 (CH), 88.4 (CH), 86.7 (CH), 79.7 (CH), 74.0 (CH), 73.1 (CH), 71.5 (CH), 70.5 (CH), 69.4 (CH), 68.5 ($CH_2$), 67.4 (CH), 64.53 ($CH_2$), 64.45 ($CH_2$), 55.40 ($CH_3$), 55.39 ($CH_3$), 53.38 (C), 48.5 (CH), 46.6 (C), 42.0 ($CH_2$), 37.2 ($CH_2$), 36.4 (C), 35.1 ($CH_2$), 34.0 (CH), 32.5 ($CH_2$), 31.74 (CH), 31.69 ($CH_2$), 31.3 ($CH_2$), 20.5 ($CH_2$), 20.4 ($CH_3$), 19.3 ($CH_3$), 12.9 ($CH_3$), 12.1 ($CH_3$) ppm; ESI-MS m/z (%) 961.4 (MNa$^+$); for $C_{50}H_{66}O_{17}Na$, calculated: 961.4198. found: 961.4209.

Example 4

Synthesis of (20R)-21-O-pentanoyl-20-methylpregn-5-ene-3β,16β,17α,21-tetraol 16-O-{2-O-(4-methoxybenzoyl)-β-D-xylopyranosyl-(1→3)-2'-O-acetyl-α-L-arabinopyranoside} (formula II, R=pentanoyl; compound 4)

Esterification with Pentanoic Acid

Esterification of (20R)-6β-methoxy-20-methyl-3α,5α-cyclopregnane-16β,17α,21-triol 16-O-{2-O-(4-methoxybenzoyl)-3,4-di-O-triethylsilyl-β-D-xylopyranosyl-(1→3)-2'-O-acetyl-4'-O-triethylsilyl-α-L-arabinopyranoside} with pentanoic acid was carried out similarly as in example 2. Silica gel column chromatography (elution with hexane-ethyl acetate; 85:15, v/v) afforded the desired ester in 89% yield, which was subsequently subjected to deprotection of functional groups.

(20R)-21-O-Pentanoyl-6β-methoxy-20-methyl-3α,
5α-cyclopregnane-16β,17α,21-triol 16-O-{2-O-(4-
methoxybenzoyl)-3,4-di-O-triethylsilyl-β-D-xylopy-
ranosyl-(1→3)-2'-O-acetyl-4'-O-triethylsilyl-α-L-
arabinopyranoside}

$^1$H NMR (400 MHz, CDCl$_3$, 25° C., TMS), δ=7.99 (d, J=8.9, 2H), 6.90 (d, J=8.9, 2H), 4.96 (m, 2H), 4.74 (d, J=5.3, 1H), 4.30 (d, J=5.7, 1H), 4.00-4.22 (m, 6H), 3.87 (s, 3H), 3.66-3.82 (m, 4H), 3.31 (s, 3H), 3.24 (m, 3H), 2.75 (m, 1H), 2.46 (t, J=7.4, 2H), 1.90 (s, 3H), 0.85-1.02 (m, 40H), 0.56-0.65 (m, 19H), 0.42 (m, 1H) ppm.

The Removal of Protective Groups from the Glycoside

The ester obtained in the previous step was treated with p-toluenesulfonic acid, according to the procedure described in example 2. The purification of the crude product by silica gel column chromatography (elution with dichloromethane-methanol; 95:5, v/v) afforded the desired saponin in 90% yield.

(20R)-21-O-Pentanoyl-20-methylpregn-5-ene-3β,
16β,17α,21-tetraol 16-O-{2-O-(4-methoxybenzoyl)-
(3-D-xylopyranosyl-(1-43)-2'-O-acetyl-α-L-ara-
binopyranoside} (compound 4)

IR(CHCl$_3$) ν=3590, 3468, 1728, 1606, 1512, 1259, 1170 cm$^{-1}$; $^1$H NMR (400 MHz, CDCl$_3$, 25° C., TMS), δ=8.00 (d, J=8.6, 2H), 6.94 (d, J=8.6, 2H), 5.34 (m, 1H), 5.05 (m, 1H), 4.94 (t, J=7.0, 1H), 4.76 (d, J=6.0, 1H), 4.37 (d, J=5.4, 1H), 4.16 (dd, J=3.9, J$_2$=11.5, 1H), 3.94-4.04 (m, 3H), 3.87 (s, 3H), 3.82 (m, 3H), 3.75 (m, 2H), 3.65 (m, 1H), 3.50 (m, 2H), 3.43 (m, 1H), 2.22 (t, J=7.3, 2H), 1.83 (s, 3H), 1.01 (s, 3H), 0.908 (t, J=7.2, 3H), 0.907 (d, J=6.7, 3H), 0.84 (s, 3H) ppm; $^{13}$C NMR (100 MHz, CDCl$_3$, 25° C., TMS), δ=173.1 (C), 169.4 (C), 166.1 (C), 164.1 (C), 140.6 (C), 132.1 (2CH), 121.5 (CH), 121.2 (C), 113.9 (2CH), 101.8 (CH), 101.4 (CH), 88.7 (CH), 86.9 (C), 79.7 (CH), 74.3 (CH), 73.6 (CH), 71.7 (CH), 70.4 (CH), 69.7 (CH), 68.4 (CH$_2$), 66.6 (CH), 64.4 (CH$_2$), 55.5 (CH$_3$), 53.4 (CH, CH$_2$), 49.7 (CH), 48.5 (CH), 46.6 (C), 42.3 (CH$_2$), 37.2 (CH$_2$), 36.4 (C), 34.9 (CH$_2$), 34.1 (CH$_2$), 33.7 (CH), 32.4 (CH), 31.8 (CH), 31.7 (CH$_2$), 31.6 (CH$_2$), 26.9 (CH$_2$), 22.2 (CH$_2$), 20.6 (CH$_3$), 19.4 (CH$_3$), 13.7 (CH$_3$), 12.9 (CH$_3$), 12.2 (CH$_3$) ppm; ESI-MS m/z (%) 911.5 (MNa$^+$); for C$_{47}$H$_{68}$O$_{16}$Na, calculated: 911.43996. found: 911.44275.

Example 5

Synthesis of (20R)-21-O-heptanoyl-20-methylpregn-
5-ene-3β,16β,17α,21-tetraol 16-O-{2-O-(4-meth-
oxybenzol)-β-D-xylopyranosyl-(1-43)-2'-O-acetyl-α-
L-arabinopyranoside} (formula II, R=heptanoyl;
compound 5)

Esterification with Heptanoic Acid

Esterification of (20R)-6β-methoxy-20-methyl-3α,5α-cyclopregnane-16β,17α,21-triol 16-O-{2-O-(4-methoxybenzoyl)-3,4-di-O-triethylsilyl-β-D-xylopyranosyl-(1→3)-2'-O-acetyl-4'-O-triethylsilyl-α-L-arabinopyranoside} with heptanoic acid was carried out similarly as in example 2. Silica gel column chromatography (elution with hexane-ethyl acetate; 85:15, v/v) afforded the desired ester in 80% yield, which was subsequently subjected to deprotection of functional groups.

(20R)-21-O-Heptanoyl-20-methyl-6β-methoxy-3α,
5α-cyclopregnan-16β,17α,21-triol 16-O-{2-O-(4-
methoxybenzoyl)-3,4-di-O-triethylsilyl-β-D-xylopy-
ranosyl-(1→3)-2'-O-acetyl-4'-O-triethylsilyl-α-L-
arabinopyranoside}

$^1$H NMR (400 MHz, CDCl$_3$, 25° C., TMS), δ=7.99 (d, J=8.8, 2H), 6.90 (d, J=8.8, 2H), 5.02 (dd, J$_1$=5.6, J$_2$=7.5, 1H), 4.93 (dd, J$_1$=5.8, J$_2$=6.2, 1H), 4.75 (d, J=5.1, 1H), 4.30 (d, J=5.3, 1H), 4.12 (m, 2H), 3.99 (m, 2H), 3.87 (s, 3H), 3.75 (t, J=6.6, 1H), 3.66 (m, 3H), 3.35 (dd, J$_1$=1.2, J$_2$=10.1, 1H), 3.31 (s, 3H), 3.25 (dd, J$_1$=7.3, J$_2$=11.5, 1H), 2.76 (m, 1H), 2.36 (t, J=7.5, 2H), 1.90 (s, 3H), 0.87-1.02 (m, 48H), 0.54-0.64 (m, 19H), 0.42 (dd, J$_1$=5.2, J$_2$=7.8, 1H) ppm.

The Removal of Protective Groups from the Glycoside

The obtained in previous step ester was treated with p-toluenesulfonic acid, according to procedure described in example 2. The purification of the crude product by silica gel column chromatography (elution with dichloromethane-methanol; 96:4, v/v) afforded desired saponin in 92% yield.

(20R)-21-O-Heptanoyl-20-methylpregn-5-ene-3β,
16β,17α,21-tetraol 16-O-{2-O-(4-methoxybenzoyl)-
β-D-xylopyranosyl-(1-3)-2'-O-acetyl-α-L-arabinopy-
ranoside} (compound 5)

IR (film) ν=3446, 1734, 1717, 1699, 1653, 1606, 1512, 1259, 1180 cm$^{-1}$; 1H NMR (400 MHz, CDCl$_3$/MeOD, 25° C., TMS), δ=7.97 (d, J=8.9, 2H), 6.91 (d, J=8.9, 2H), 5.29 (m, 1H), 5.02 (dd, J$_1$=6.4, J$_2$=8.4, 1H), 4.91 (dd, J$_1$=6.7, J$_2$=7.7, 1H), 4.65 (d, J=6.5, 1H), 4.29 (d, J=6.4, 1H), 4.01-4.08 (m, 2H), 3.91-3.97 (m, 2H), 3.86 (m, 1H), 3.84 (s, 3H), 3.60-3.71 (m, 5H), 3.42 (m, 2H), 3.34 (dd, J$_1$=8.6, J$_2$=11.7, 1H), 1.72 (s, 3H), 0.97 (s, 3H), 0.90 (d, J=7.0, 3H), 0.86 (m, 3H), 0.80 (s, 3H) ppm; $^{13}$C NMR (100 MHz, CDCl$_3$/MeOD, 25° C., TMS), δ=174.0 (C), 169.5 (C), 165.7 (C), 163.8 (C), 140.6 (C), 132.0 (2CH), 121.6 (C), 121.4 (CH), 113.7 (2CH), 102.3 (CH), 101.7 (CH), 88.5 (CH), 86.7 (C), 79.7 (CH), 74.0 (CH), 73.2 (CH), 71.5 (CH), 70.5 (CH), 69.4 (CH), 68.3 (CH$_2$), 67.2 (CH), 64.5 (CH$_2$), 64.3 (CH$_2$), 55.4 (CH$_3$), 49.7 (CH), 48.5 (CH), 46.5 (C), 42.0 (CH$_2$), 37.2 (CH$_2$), 36.4 (C), 35.0 (CH$_2$), 34.3 (CH$_2$), 33.7 (CH), 32.4 (CH$_2$), 31.73 (CH$_2$), 31.68 (CH), 31.4 (CH$_2$), 28.7 (CH$_2$), 26.0 (CH$_2$), 24.8 (CH$_2$), 22.4 (CH$_2$), 20.5 (CH$_2$), 20.4 (CH$_3$), 19.3 (CH$_3$), 13.9 (CH$_3$), 12.8 (CH$_3$), 12.0 (CH$_3$) ppm; ESI-MS m/z (%) 939.5 (MNa$^+$); for C$_{49}$H$_{72}$O$_{16}$Na, calculated: 939.47126. found: 939.47337.

Example 6

Synthesis of (20R)-21-O-(undec-10-enoyl)-20-meth-
ylpregn-5-ene-3β,16β,17α,21-tetraol 16-O-{2-O-(4-
methoxybenzoyl)-β-D-xylopyranosyl-(13)-2'-O-
acetyl-α-L-arabinopyranoside} (formula II,
R=undec-10-enoyl; compound 6)

Esterification with Undec-10-Enoic Acid

Esterification of (20R)-6β-methoxy-20-methyl-3α,5α-cyclopregnane-16β,17α,21-triol 16-O-{2-O-(4-methoxybenzoyl)-3,4-di-O-triethylsilyl-β-D-xylopyranosyl-(1→3)-2'-O-acetyl-4'-O-triethylsilyl-α-L-arabinopyranoside} with undec-10-enoic acid was carried out similarly as in example 2. Silica gel column chromatography (elution with hexane-ethyl acetate; 7:1, v/v) afforded the desired ester in 63% yield, which was subsequently subjected to deprotection of functional groups.

(20R)-21-O-(Undec-10-enoyl)-20-methyl-6β-methoxy-3α,5α-cyclopregnan-16β,17α,21-triol 16-O-{2-O-(4-methoxybenzoyl)-3,4-di-O-triethylsilyl-β-D-xylopyranosyl-(1→3)-2'-O-acetyl-4'-O-triethylsilyl-α-L-arabinopyranoside}

$^1$H NMR (400 MHz, CDCl$_3$, 25° C., TMS), δ=7.99 (d, J=8.7, 2H), 6.90 (d, J=8.7, 2H), 5.82 (m, 1H), 4.93-5.02 (m, 4H), 4.75 (m, 1H), 4.31 (t, 1H), 4.12 (m, 2H), 4.01 (m, 2H), 3.87 (s, 3H), 3.62-3.87 (m, 4H), 3.36 (m, 2H), 3.31 (s, 3H), 3.25 (m, 1H), 2.5 (m, 1H), 2.23 (m, 2H), 1.91 (s, 3H), 0.89-1.02 (m, 40H), 0.56-0.64 (m, 19H), 0.42 (m 1H) ppm.

The Removal of Protective Groups from the Glycoside

The ester obtained in the previous step was treated with p-toluenesulfonic acid, according to procedure described in example 2. The purification of the crude product by silica gel column chromatography (elution with dichloromethane-methanol; 95:5, v/v) afforded the desired saponin in 95% yield.

(20R)-21-O-(Undec-10-enoyl)-20-methylpregn-5-ene-3β,16β,17α,21-tetraol 16-O-{2-O-(4-methoxybenzoyl)-β-D-xylopyranosyl-(1→3)-O-acetyl-α-L-arabinopyranoside} (compound 6)

IR (KBr) ν=3448, 1735, 1719, 1606, 1512, 1257, 1047 cm$^{-1}$; $^1$H NMR (400 MHz, CDCl$_3$/MeOD, 25° C., TMS), δ=7.95 (d, J=8.9, 2H), 6.89 (d, J=8.9, 2H), 5.77 (m, 1H), 5.27 (d, J=4.6, 1H), 5.01 (dd, J$_1$=6.7, J$_2$=8.6, 1H), 4.95 (dd, J$_1$=1.9, J$_2$=17.1, 1H), 4.88 (m, 2H), 4.61 (d, J=6.6, 1H), 4.25 (d, J=6.6, 1H), 4.02 (m, 2H), 3.93 (m, 2H), 3.83 (s, 4H), 3.59-3.67 (m, 4H), 3.42 (m, 2H), 3.30 (m, 1H), 2.00 (m, 2H), 1.68 (s, 3H), 0.95 (s, 3H), 0.89 (d, J=7.0, 3H), 0.77 (s, 3H); $^{13}$C NMR (100 MHz, CDCl$_3$/MeOD, 25° C., TMS), δ=174.0 (C), 169.4 (C), 165.6 (C), 163.7 (C), 140.5 (C), 139.0 (CH), 131.9 (2CH), 121.6 (C), 121.3 (CH), 114.0 (CH$_2$), 113.6 (2CH), 102.3 (CH), 101.7 (CH), 88.3 (CH), 86.6 (C), 79.6 (CH), 73.9 (CH), 73.1 (CH), 71.3 (CH), 70.4 (CH), 69.3 (CH), 68.3 (CH$_2$), 67.3 (CH), 64.6 (CH$_2$), 64.4 (CH$_2$), 55.3 (CH$_3$), 49.6 (CH), 48.4 (CH), 46.5 (C), 41.9 (CH$_2$), 37.1 (CH$_2$), 36.3 (C), 35.0 (CH$_2$), 34.2 (CH$_2$), 33.6 (CH$_2$, CH), 32.3 (CH$_2$), 31.64 (CH), 31.60 (CH$_2$), 31.2 (CH$_2$), 29.2 (CH$_2$), 29.1, (CH$_2$), 29.0 (CH$_2$), 28.9 (CH$_2$), 28.8 (CH$_2$), 24.8 (CH$_2$), 20.4 (CH$_2$), 20.3 (CH$_3$), 19.2 (CH$_3$), 12.7 (CH$_3$), 11.9 (CH$_3$) ppm; ESI-MS m/z (%) 993.5 (MNa$^+$); for C$_{53}$H$_{78}$O$_{16}$Na, calculated: 993.5188. found: 993.5186.

Example 7

Synthesis of (20R)-21-O-[(E)-but-2-enoyl]-20-methylpregn-5-ene-3β,16β,17α,21-tetraol 16-O-{2-O-(4-methoxybenzoyl)-β-D-xylopyranosyl-(1→3)-2'-O-acetyl-α-L-arabinopyranoside} (formula II, R=(E)-but-2-enoyl; compound 7)

Esterification with (E)-but-2-enoic acid

Esterification of (20R)-6-methoxy-20-methyl-3α,5α-cyclopregnane-16β,17α,21-triol 16-O-{2-O-(4-methoxybenzoyl)-3,4-di-O-triethylsilyl-β-D-xylopyranosyl-(1→3)-2'-O-acetyl-4'-O-triethylsilyl-α-L-arabinopyranoside} with (E)-but-2-enoic acid was carried out similarly as in example 2. Silica gel column chromatography (elution with hexane-ethyl acetate; 82:18, v/v) afforded the desired ester in 95% yield, which was subsequently subjected to deprotection of functional groups.

(20R)-21-O-[(E)-But-2-enoyl]-6β-methoxy-20-methyl-3α,5α-cyclopregnane-16β,17α,21-triol 16-O-{2-O-(4-methoxybenzoyl)-3,4-di-O-triethylsilyl-β-D-xylopyranosyl-(1→3)-2'-O-acetyl-4'-O-triethylsilyl-α-L-arabinopyranoside

[$^1$H NMR (400 MHz, CDCl$_3$, 25° C., TMS), δ=7.98 (d, J=8.7, 2H), 7.08 (dd J$_1$=6.9, J$_2$=15.5, 1H), 6.90 (d, J=8.7, 2H), 5.77 (dq, J$_1$=1.7, J$_2$=15.5, 1H), 5.03 (m, 1H), 4.94 (t, 1H), 4.77 (m, 1H), 4.31 (t, 1H), 4.00-4.18 (m, 4H), 3.87 (s, 3H), 3.63-3.74 (m, 4H), 3.36 (m, 2H), 3.31 (s, 3H), 3.24 (m, 1H), 2.75 (m, 1H), 1.89 (s, 3H), 1.84 (d, J=1.7, 3H), 0.87-1.02 (m, 34H), 0.52-0.66 (m, 19H), 0.42 (m, 1H) ppm.

The Removal of Protective Groups from the Glycoside

The ester obtained in the previous step was treated with p-toluenesulfonic acid, according to procedure described in example 2. The purification by silica gel column chromatography (elution with dichloromethane-methanol; 94:6, v/v) afforded the desired saponin in 94% yield.

(20R)-21-O-[(E)-But-2-enoyl]-20-methylpregn-5-ene-3β,16β,17α,21-tetraol 16-O-{2-O-(4-methoxybenzoyl)β-D-xylopyranosyl-(1→3)-2'-O-acetyl-α-L-arabinopyranoside} (compound 7)

IR (KBr) ν=3445, 1748, 1715, 1606, 1513, 1259 cm$^{-1}$; $^1$H NMR (400 MHz, CDCl$_3$/MeOD, 25° C., TMS), δ=7.94 (d, J=8.9, 2H), 6.88 (d, J=8.9, 2H), 6.86 (dd, J=6.9, J$_2$=15.5, 1H), 5.70, (dq, J=1.7, J$_2$=15.5, 1H), 5.26 (m, 1H), 5.01 (dd, J=6.8, J$_2$=8.8, 1H), 4.87 (dd, J=6.98 J$_2$=8.1, 1H), 4.59 (d, J=6.8, 1H), 4.25 (d, J=6.8 1H), 4.07 (dd, J=6.4, J$_2$=11.0, 1H), 4.00 (dd, J$_1$=4.6, J$_2$=11.7, 1H), 3.86-3.95 (m, 3H), 3.85 (s, 3H), 3.57-3.67 (m, 4H), 3.41 (m, 2H), 3.33 (t, d, J=1.6, 1H), 3.28 (dd, J$_1$=8.8, J$_2$=11.7, 1H), 1.81 (dd, J$_1$=1.7, J$_2$=6.9, 1H), 1.63 (s, 3H), 0.94 (s, 3H), 0.90 (d, J=7.0, 3H), 0.77 (s, 3H) ppm; $^{13}$C NMR (100 MHz, CDCl$_3$, 25° C., TMS), δ=169.4 (C), 166.7 (C), 165.6 (C), 163.7 (C), 145.1 (CH), 140.5 (C), 131.9 (2CH), 122.2 (CH), 121.7 (C), 121.3 (CH), 113.6 (2CH), 102.4 (CH), 101.8 (CH), 88.1 (CH), 86.5 (C), 79.6 (CH), 74.0 (CH), 73.1 (CH), 71.3 (CH), 70.5 (CH), 69.3 (CH), 68.0 (CH$_2$), 67.5 (CH), 64.8 (CH$_2$), 64.5 (CH$_2$), 55.3 (CH$_3$), 49.6 (CH), 48.4 (CH), 46.5 (C), 41.8 (CH$_2$), 37.1 (CH$_2$), 36.3 (C), 35.1 (CH$_2$), 33.8 (CH), 32.3 (CH$_2$), 31.63 (CH), 31.59 (CH$_2$), 31.1 (CH$_2$), 20.4 (CH$_2$), 20.3 (CH$_3$), 19.1 (CH$_3$), 17.8 (CH$_3$), 12.7 (CH$_3$), 11.8 (CH$_3$) ppm; ESI-MS m/z (%) 895.4 (MNa$^+$); for C$_{46}$H$_{64}$O$_{16}$Na, calculated: 895.4092. found: 895.4117.

Example 8

Synthesis of (20R)-21-O-hept-6-enoyl-20-methylpregn-5-ene-3β,16β,17α,21-tetraol 16-O-{2-O-(4-methoxybenzol)-β-D-xylopyranosyl-(1→3)-2'-O-acetyl-α-L-arabinopyranoside} (formula H, R=hept-6-enoyl; compound 8)

Esterification with hept-6-enoic acid

Esterification of (20R)-6β-methoxy-20-methyl-3α,5α-cyclopregnane-16β,17α,21-triol 16-O-{2-O-(4-methoxybenzoyl)-3,4-di-O-triethylsilyl-β-D-xylopyranosyl-(13)-2'-O-acetyl-4'-O-triethylsilyl-α-L-arabinopyranoside} with hept-6-enoic acid was carried out similarly as in example 2. Silica gel column chromatography (elution with hexane-ethyl acetate; 84:16, v/v) afforded the desired ester in 82% yield, which was subsequently subjected to deprotection of functional groups.

(20R)-21-O-Hept-6-enoyl-20-methyl-6β-methoxy-
3α,5α-cyclopregnan-16β,17α,21-triol 16-O-{2-O-
(4-methoxybenzoyl)-3,4-di-O-triethylsilyl-β-D-xy-
lopyranosyl-(1→3)-2'-O-acetyl-4'-O-triethylsilyl-
α-L-arabinopyranoside}

$^1$H NMR (400 MHz, CDCl$_3$, 25° C., TMS), δ=7.99 (d, J=8.9, 2H), 6.90 (d, J=8.9, 2H), 5.80 (m, 1H), 4.92-5.04 (m, 4H), 4.75 (d, J=5.0, 1H), 4.31 (d, J=5.1, 1H), 4.12 (m, 2H), 3.96-4.01 (m, 2H), 3.87 (s, 3H), 3.85 (m, 1H), 3.74 (dd, J$_1$=6.5, J$_2$=6.6, 1H), 3.62-3.71 (m, 4H), 3.35 (dd, J$_1$=2.0, J$_2$=11.7, 1H), 3.31 (s, 3H), 3.25 (dd, J$_1$=7.2, J$_2$=11.7, 1H), 2.76 (m, 1H), 2.43 (dd, J$_1$=7.4, J$_2$=7.6, 1H), 2.37 (t, J=7.5, 2H), 1.90 (s, 3H), 0.87-0.98 (m, 38H), 0.56-0.63 (m, 19H), 0.42 (dd, J$_1$=5.2, J$_2$=7.8, 1H) ppm.

The Removal of Protective Groups from the Glycoside

The obtained in previous step ester was treated with p-toluenesulfonic acid, according to procedure described in example 2. The purification of the crude product by silica gel column chromatography (elution with dichloromethane-methanol, 95:5, v/v) afforded desired saponin in 77% yield.

(20R)-21-O-Hept-6-enoyl-20-methylpregn-5-ene-3β,
16β,17α,21-tetraol 16-O-{2-O-(4-methoxybenzoyl)
β-D-xylopyranosyl-(1→3)-O-acetyl-α-L-arabinopyra-
noside} (compound 8)

IR (KBr) ν=3448, 1719, 1606, 1512, 1258, 1046 cm$^{-1}$; $^1$H NMR (400 MHz, CDCl$_3$/MeOD, 25° C., TMS), δ=7.93 (d, J=8.9, 2H), 6.97 (d, J=8.9, 2H), 5.67-5.77 (m, 1H), 5.25 (d, J=4.2, 1H), 4.84-5.00 (m, 4H), 4.58 (d, J=6.8; 1H), 4.23 (d, J=6.9, 1H), 3.96-4.03 (m, 2H), 3.93 (m, 1H), 3.90 (dd, J$_1$=3.6, J$_2$=12.4, 1H), 3.81 (s, 3H), 3.80 (dd, J=3.4, J$_2$=10.8, 1H) 3.56-3.65 (m, 4H), 3.40 (m, 2H), 3.32 (m, 1H), 2.17 (m, 2H), 2.16 (t, dd, J=7.5, 2H), 1.98 (s, 3H), 0.93 (s, 3H), 0.86 (d, J=7.0, 3H), 0.75 (s, 3H) ppm; $^{13}$C NMR (100 MHz, CDCl$_3$/MeOD, 25° C., TMS), δ=173.9 (C), 169.3 (C), 165.6 (C), 163.6 (C), 140.5 (C), 138.1 (CH), 131.8 (2CH), 128.2 (CH), 121.7 (C), 121.3 (CH), 114.6 (CH$_2$), 113.6 (2CH), 102.3 (CH), 101.8 (CH), 88.1 (CH), 86.5 (C), 79.5 (CH), 73.9 (CH), 73.1 (CH), 71.2 (CH), 70.4 (CH), 69.3 (CH), 68.2 (CH$_2$), 67.4 (CH), 64.7 (CH$_2$), 64.4 (CH$_2$), 55.3 (CH$_3$), 49.6 (CH), 48.3 (CH), 46.4 (C), 41.8 (CH$_2$), 37.0 (CH$_2$), 36.3 (C), 34.9 (CH$_2$), 34.0 (CH$_2$), 33.7 (CH), 33.1 (CH$_2$), 32.2 (CH$_2$), 31.61 (CH), 31.57 (CH$_2$), 31.1 (CH$_2$), 28.1 (CH$_2$), 24.1 (CH$_2$), 20.4 (CH$_2$), 20.2 (CH$_3$), 19.1 (CH$_3$), 12.7 (CH$_3$), 11.8 (CH$_3$), ppm; ESI-MS m/z (%) 937.5 (MNa$^+$); for C$_{49}$H$_{70}$O$_{16}$Na, calculated: 937.4562. found: 937.4597.

Example 9

Synthesis of (20R)-21-O-tetradecanoyl-20-methyl-
pregn-5-ene-3β,16β,17α,21-tetraol 16-O-{2-O-(4-
methoxybenzoyl)β-D-xylopyranosyl-(1-43)-2'-O-
acetyl-α-L-arabinopyranoside} (formula II,
R=tetradecanoyl; compound 9)

Esterification with myristic (tetradecanoic) acid

Esterification of (20R)-6β-methoxy-20-methyl-3α,5α-cyclopregnane-16β,17α,21-triol 16-O-{2-O-(4-methoxybenzoyl)-3,4-di-O-triethylsilyl-β-D-xylopyranosyl-(1→3)-2'-O-acetyl-4'-O-triethylsilyl-α-L-arabinopyranoside} with myristic acid was carried out similarly as in example 2. Silica gel column chromatography (elution with hexane-ethyl acetate, 86:14, v/v) afforded the desired ester in 98% yield, which was subsequently subjected to deprotection of functional groups.

(20R)-21-O-Tetradecanoyl-20-methyl-6β-methoxy-
3α,5α-cyclopregnan-16β,17α,21-triol 16-O-{2-O-
(4-methoxybenzoyl)-3,4-di-O-triethylsilyl-β-D-xy-
lopyranosyl-(1→3)-2'-O-acetyl-4'-O-triethylsilyl-α-
L-arabinopyranoside}

$^1$H NMR (400 MHz, CDCl$_3$, 25° C., TMS), δ=7.99 (d, J=8.8, 2H), 6.90 (d, J=8.8, 2H), 5.02 (dd, J$_1$=5.6, J$_2$=7.5, 1H), 4.93 (dd, J$_1$=6.0, J$_2$=6.2, 1H), 4.74 (d, J 5.2, 1H), 4.30 (d, J=5.4, 1H), 4.12 (m, 2H), 3.99 (m, 2H), 3.87 (s, 3H), 3.84 (dd, J$_1$=4.6, J$_2$=11.7, 1H), 3.74 (dd, J$_1$=6.4, J$_2$=6.7, 1H), 3.60-3.73 (m, 3H), 3.35 (dd, J$_1$=1.5, J$_2$=11.6, 1H), 3.31 (s, 3H), 3.24 (dd, J$_1$=7.4, J$_2$=11.6, 1H), 2.75 (m, 1H), 2.35 (m, 2H), 2.23 (m, 3H), 1.90 (s, 3H), 1.26 (bs, 19H), 1.02 (s, 3H), 0.87-0.98 (m, 41H), 0.52-0.65 (m, 19H), 0.42 (dd, J$_1$=5.2, J$_2$=7.8, 1H) ppm.

The Removal of Protective Groups from the Glycoside

The obtained in previous step ester was treated with p-toluenesulfonic acid, according to procedure described in example 2. The purification of the crude product by silica gel column chromatography (elution with dichloromethane-methanol; 94.5:5.5, v/v) afforded desired saponin in 89% yield.

(20R)-21-O-Tetradecanoyl-20-methylpregn-5-ene-3
(3β,16β,17α,21-tetraol 16-O-{2-O-(4-methoxyben-
zoyl)-β-D-xylopyranosyl-(1→3)-2'-O-acetyl-α-L-
arabinopyranoside} (compound 9)

IR(CHCl$_3$) ν=3580, 1728, 1606, 1512, 1259, 1170 cm$^{-1}$; $^1$H NMR (400 MHz, CDCl$_3$, 25° C., TMS), δ=7.99 (d, J=8.8, 2H), 6.93 (d, J=8.8, 2H), 5.33 (d, J=4.6, 1H), 5.05 (dd, J$_1$=5.7, J$_2$=7.6, 1H), 4.95 (dd, J$_1$=7.0, J$_2$=7.4, 1H), 4.74 (d, J=6.3, 1H), 4.36 (d, J=5.7, 1H), 4.15 (dd, J$_1$=4.3, J$_2$=11.7, 1H), 4.01 (m, 2H), 3.95 (dd, J$_1$=4.9, J$_2$=12.2, 1H), 3.87 (s, 3H), 3.72-3.84 (m, 3H), 3.64 (m, 1H), 3.45 (m, 3H), 3.42 (dd, J$_1$=8.6, J$_2$=11.7, 1H), 2.21-2.23 (m, 5H), 1.80 (s, 3H), 1.26 (bs, 19H), 1.01 (s, 3H), 0.91 (d, J=7.0, 3H), 0.89 (t, J=6.8, 3H), 0.83 (s, 3H) ppm; $^{13}$C NMR (100 MHz, CDCl$_3$, 25° C., TMS), δ=173.7 (C), 169.5 (C), 166.1 (C), 164.0 (C), 140.6 (C), 132.1 (2CH), 121.5 (CH), 121.2 (C), 113.9 (2CH), 101.9 (CH), 101.4 (CH), 88.7 (CH), 86.9 (C), 79.8 (CH), 74.3 (CH), 73.6 (CH), 71.7 (CH), 70.4 (CH), 69.7 (CH), 68.4 (CH$_2$), 64.4 (CH$_2$, CH), 55.5 (CH$_3$), 49.7 (CH), 48.5 (CH), 46.5 (C), 42.3 (CH$_2$), 37.2 (CH$_2$), 36.4 (C), 34.9 (CH$_2$), 34.4 (CH$_2$), 33.7 (CH), 32.4 (CH$_2$), 31.9 (CH$_2$), 31.8 (CH), 31.7 (CH$_2$), 31.6 (CH$_2$), 29.7 (2CH$_2$), 29.65 (2CH$_2$), 29.61 (CH$_2$), 29.5 (CH$_2$), 29.4 (CH$_2$), 29.3 (CH$_2$), 29.1 (CH$_2$), 24.9 (CH$_2$), 22.7 (CH$_2$), 20.6 (CH$_3$, CH$_2$), 19.4 (CH$_3$), 14.1 (CH$_3$), 12.9 (CH$_3$), 12.2 (CH$_3$) ppm; ESI-MS m/z (%) 1037.6 (MNa$^+$); for C$_{56}$H$_{86}$O$_{16}$Na, calculated: 1037.5814. found: 1037.5785.

Example 10

Synthesis of (20R)-21-O-octadecanoyl-20-methyl-
pregn-5-ene-3β-3β,16β,17α,21-tetraol 16-O-{2-O-
(4-methoxybenzol)-β-D-xylopyranosyl-(1→3)-2'-O-
acetyl-α-L-arabinopyranoside} (formula II,
R=octadecanoyl; compound 10)

Esterification with Stearic (Octadecanoic) Acid

Esterification of (20R)-6β-methoxy-20-methyl-3α,5α-cyclopregnane-16β,17α,21-triol 16-O-{2-O-(4-methoxybenzoyl)-3,4-di-O-triethylsilyl-β-D-xylopyranosyl-(13)-2'-O-acetyl-4'-O-triethylsilyl-α-L-arabinopyranoside} with stearic acid was carried out similarly as in example 2. Silica gel column chromatography (elution with hexane-ethyl acetate (88:12, v/v)) afforded the desired ester in 92% yield, which was subsequently subjected to deprotection of functional groups.

(20R)-21-O-Octadecanoyl-20-methyl-6β-methoxy-3α,5α-cyclopregnan-16β,17α,21-triol 16-O-{2-O-(4-methoxybenzoyl)-3,4-di-O-triethylsilyl-β-D-xylopyranosyl-(1-43)-2'-O-acetyl-4'-O-triethylsilyl-α-L-arabinopyranoside}

$^1$H NMR (400 MHz, CDCl$_3$, 25° C., TMS), δ=7.99 (d, J=8.8, 2H), 6.90 (d, J=8.8, 2H), 5.02 (dd, J$_1$=5.5, J$_2$=7.7, 1H), 4.93 (dd, J$_1$=5.8, J$_2$=6.4, 1H), 4.74 (d, J=5.2, 1H), 4.30 (d, J=5.4, 1H), 4.12 (m, 2H), 3.99 (m, 2H), 3.87 (s, 3H), 3.85 (dd, J$_1$=4.7, J$_2$=11.8, 1H), 3.75 (dd, J$_1$=6.6, J$_2$=6.7, 1H), 3.62-3.71 (m, 3H), 3.35 (dd, =1.8, J$_2$=11.7, 1H), 3.31 (s, 3H), 3.25 (dd, J$_1$=7.4, J$_2$=11.6, 1H), 2.75 (m, 1H), 2.35 (t, J=7.5, 2H), 1.90 (s, 3H), 1.26 (bs, 26H), 1.02 (s, 3H), 0.87-0.98 (m, 42H), 0.52-0.65 (m, 19H), 0.42 (dd, J$_1$=5.2, J$_2$=7.8, 1H) ppm.

The Removal of Protective Groups from the Glycoside

The obtained in previous step ester was treated with p-toluenesulfonic acid, according to procedure described in Example 2. The purification of the crude product by silica gel column chromatography (elution with dichloromethane-methanol; 96.5:3.5, v/v) afforded desired saponin in 80% yield.

(20R)-21-O-Octadecanoyl-20-methylpregn-5-ene-3β,16β,17α,21-tetraol 16-O-{2-O-(4-methoxybenzoyl)-β-D-xylopyranosyl-(1→3)-2'-O-acetyl-α-L-arabinopyranoside} (compound 10)

IR(CHCl$_3$) v=3467, 1728, 1606, 1512, 1259, 1170; $^1$H NMR (400 MHz, CDCl$_3$, 25° C., TMS), δ=7.99 (d, J=8.8, 2H), 6.93 (d, J=8.8, 2H), 5.33 (d, J=4.4, 1H), 5.05 (dd, J$_1$=5.8, J$_2$=7.4, 1H), 4.95 (dd, J$_1$=6.8, J$_2$=7.6, 1H), 4.74 (d, J=6.4, 1H), 4.36 (d, J=5.7, 1H), 4.15 (dd, J$_1$=4.4, J$_2$=11.7, 1H), 4.01 (m, 2H), 3.96 (dd, J$_1$=4.7, J$_2$=12.0, 1H), 3.87 (s, 3H), 3.73-3.87 (m, 4H), 3.64 (m, 3H), 3.32-3.51 (m, 4H), 2.17-2.23 (m, 5H), 1.82 (s, 3H), 1.26 (bs, 26H), 1.01 (s, 3H), 0.91 (d, J=6.9, 3H), 0.89 (t, J=7.0, 3H), 0.83 (s, 3H) ppm; $^{13}$C NMR (100 MHz, CDCl$_3$, 25° C., TMS), δ=173.7 (C), 169.5 (C), 166.0 (C), 164.0 (C), 140.6 (C), 132.1 (2CH), 121.5 (CH), 121.2 (C), 113.9 (2CH), 101.9 (CH), 101.5 (CH), 88.7 (CH), 86.9 (C), 79.8 (CH), 74.4 (CH), 73.6 (CH), 71.7 (CH), 70.4 (CH), 69.7 (CH), 68.4 (CH$_2$), 66.7 (CH), 64.5 (CH$_2$), 63.7 (CH$_2$), 55.5 (CH$_3$), 49.7 (CH), 48.5 (CH), 46.5 (C), 42.3 (CH$_2$), 37.2 (CH$_2$), 36.4 (C), 35.0 (CH$_2$), 34.4 (CH$_2$), 33.7 (CH), 32.4 (CH$_2$), 31.9 (CH$_2$), 31.8 (CH), 31.7 (CH$_2$), 31.6 (CH$_2$), 29.7 (4CH$_2$), 29.65 (3CH$_2$), 29.6 (CH$_2$), 29.5 (CH$_2$), 29.4 (CH$_2$), 29.3 (CH$_2$), 29.1 (CH$_2$), 24.9 (CH$_2$), 22.7 (CH$_2$), 20.5 (CH$_2$, CH$_3$), 19.4 (CH$_3$), 14.1 (CH$_3$), 12.9 (CH$_3$), 12.2 (CH$_3$) ppm; ESI-MS m/z (%) 1093.7 (MNa$^+$).

Example 11

Synthesis of (20R)-21-O-dodecanoyl-20-methylpregn-5-ene-3β,16β,17α,21-tetraol 16-O-{2-O-(4-methoxybenzol)-β-D-xylopyranosyl-(1→3)-2'-O-acetyl-α-L-arabinopyranoside} (formula II, R=dodecanoyl; compound 11)

Esterification with Lauric (Dodecanoic) Acid

Esterification of (20R)-β-methoxy-20-methyl-3α,5α-cyclopregnane-16β,17α,21-triol 16-O-{2-O-(4-methoxybenzoyl)-3,4-di-O-triethylsilyl-β-D-xylopyranosyl-(1→3)-2'-O-acetyl-4'-O-triethylsilyl-α-L-arabinopyranoside} with lauric acid was carried out similarly as in example 2. Silica gel column chromatography (elution with hexane-ethyl acetate (88:12, v/v)) afforded the desired ester in 78% yield, which was subsequently subjected to deprotection of functional groups.

(20R)-21-O-Dodecanoyl-20-methyl-6β-methoxy-3α,5α-cyclopregnan-16β,17α,21-triol 16-O-{2-O-(4-methoxybenzoyl)-3,4-di-O-triethylsilyl-β-D-xylopyranosyl-(1→3)-2'-O-acetyl-4'-O-triethylsilyl-α-L-arabinopyranoside}

$^1$H NMR (400 MHz, CDCl$_3$, 25° C., TMS), δ=7.99 (d, J=8.8, 2H), 6.90 (d, J=8.8, 2H), 5.02 (dd, J=5.6, J$_2$=7.6, 1H), 4.93 (dd, J=6.0, J$_2$=6.2, 1H), 4.74 (d, J=5.2, 1H), 4.30 (d, J=5.3, 1H), 4.12 (m, 2H), 3.98 (m, 2H), 3.87 (s, 3H), 3.84 (dd, =4.8, J$_2$=6.9, 1H), 3.74 (dd, J$_1$=6.6, J$_2$=6.7, 1H), 3.64 (m, 3H), 3.35 (dd, J=1.8, J$_2$=11.7, 1H), 3.31 (s, 3H), 3.24 (dd, J$_1$=7.4, J$_2$=11.5, 1H), 2.75 (m, 1H), 2.34 (m, 2H), 2.23 (m, 3H), 1.90 (s, 3H), 1.26 (bs, 18H), 0.87-1.02 (m, 43H), 0.54-0.64 (m, 19H), 0.42 (dd, J$_1$=5.2, J$_2$=7.8, 1H) ppm.

The Removal of Protective Groups from the Glycoside

The obtained in previous step ester was treated with p-toluenesulfonic acid, according to procedure described in example 2. The purification of the crude product by silica gel column chromatography (elution with dichloromethane-methanol; 95:5, v/v) afforded desired saponin in 95% yield.

(20R)-21-O-Dodecanoyl-20-methylpregn-5-ene-3β,16β,17α,21-tetraol 16-O-{2-O-(4-methoxybenzoyl)-β-D-xylopyranosyl-(1→43)-2'-O-acetyl-α-L-arabinopyranoside}(compound 11)

IR(CHCl$_3$) v=3579, 1727, 1606, 1512, 1259, 1170 cm$^{-1}$; $^1$H NMR (400 MHz, CDCl$_3$, 25° C., TMS), δ=7.92 (d, J=8.9, 2H), 6.92 (d, J=8.9, 2H), 5.33 (d, J=4.6, 1H), 5.05 (dd, J$_1$=5.9, J$_2$=7.8, 1H), 4.96 (dd, J$_1$=6.6, J$_2$=7.9, 1H), 4.72 (d, J=6.5, 1H), 4.34 (d, J=5.9, 1H), 4.14 (m, 1H), 3.94-4.05 (m, 3H), 3.87 (s, 3H), 3.81-3.87 (m, 2H), 3.71-3.78 (m, 3H), 3.64 (m, 1H), 3.46-3.51 (m, 3H), 3.40 (dd, J$_1$=8.7, J$_2$=11.7, 1H), 2.28 (m, 2H), 2.18-2.23 (m, 5H), 1.78 (s, 3H), 1.26 (bs, 18H) 1.01 (s, 3H), 0.91 (d, J=7.0, 3H), 0.89 (t, J=7.0, 3H), 0.83 (s, 3H) ppm; $^{13}$C NMR (100 MHz, CDCl$_3$, 25° C., TMS), δ=173.7 (C), 169.5 (C), 166.0 (C), 164.0 (C), 140.6 (C), 132.1 (2CH), 121.5 (CH), 121.3 (C), 113.8 (2CH), 102.0 (CH), 101.5 (CH), 88.7 (CH), 86.9 (C), 79.9 (CH), 74.4 (CH), 73.6 (CH), 71.7 (CH), 70.4 (CH), 69.7 (CH), 68.4 (CH$_2$), 66.8 (CH), 64.5 (CH$_2$), 63.8 (CH$_2$), 55.5 (CH$_3$), 49.7 (CH), 48.5 (CH), 46.5 (C), 42.2 (CH$_2$), 37.2 (CH$_2$), 36.4 (C), 35.0 (CH$_2$), 34.3 (CH$_2$), 33.7 (CH), 32.4 (CH$_2$), 31.9 (CH$_2$), 31.8 (CH), 31.7 (CH$_2$), 31.6 (CH$_2$), 29.6 (2CH$_2$), 29.5 (CH$_2$), 29.3 (CH$_2$), 29.2 (CH$_2$), 29.1 (CH$_2$), 24.9 (CH$_2$), 22.7 (CH$_2$), 20.54 (CH$_2$), 20.51 (CH$_3$), 19.4 (CH$_3$), 14.1 (CH$_3$), 12.9 (CH$_3$), 12.2 (CH$_3$) ppm; ESI-MS m/z (%) 1009.6 (MNa$^+$); for C$_{54}$H$_{82}$O$_{16}$Na, calculated: 1009.5501. found: 1009.5463.

Example 12

Synthesis of (20R)-21-O-nonanoyl-20-methylpregn-5-ene-3β,16β,17α,21-tetraol 16-O-{2-O-(4-methoxybenzol)-β-D-xylopyranosyl-(1→3)-2'-O-acetyl-α-L-arabino-pyranoside} (formula II, R=nonanoyl; compound 12)

Esterification with Nonanoic Acid

Esterification of (20R)-6β-methoxy-20-methyl-3α,5α-cyclopregnane-16β,17α,21-triol 16-O-{2-O-(4-methoxybenzoyl)-3,4-di-O-triethylsilyl-β-D-xylopyranosyl-(1→3)-2'-O-acetyl-4'-O-triethylsilyl-α-L-arabinopyranoside} with nonanoic acid was carried out similarly as in example 2. Silica gel column chromatography (elution with hexane-ethyl acetate (86:14, v/v)) afforded the desired ester in 85% yield, which was subsequently subjected to deprotection of functional groups.

(20R)-21-O-Nonanoyl-20-methyl-6β-methoxy-3α, 5α-cyclopregnan-16β,17α,21-triol 16-O-{2-O-(4-methoxybenzoyl)-3,4-di-O-triethylsilyl-β-D-xylopyranosyl-(1→3)-2'-O-acetyl-4'-O-triethylsilyl-α-L-arabinopyranoside}

$^1$H NMR (400 MHz, CDCl$_3$, 25° C., TMS), δ=7.99 (d, J=8.8, 2H), 6.90 (d, J=8.8, 2H), 5.02 (dd, J=5.6, J$_2$=7.5, 1H), 4.93 (dd, J$_1$=6.0, J$_2$=6.0, 1H), 4.74 (d, J=5.1, 1H), 4.30 (d, J=5.2, 1H), 4.10-4.14 (m, 2H), 3.97-4.01 (m, 2H), 3.87 (s, 3H), 3.82 (m, 1H), 3.74 (m, 1H), 3.62-3.71 (m, 3H), 3.35 (m, 1H), 3.31 (s, 3H), 3.24 (dd, J$_1$=7.4, J$_2$=11.5, 1H), 2.75 (m, 1H), 2.30-2.35 (m, 2H), 1.90 (s, 3H), 1.22 (bs, 12H), 0.87-1.02 (m, 44H), 0.54-0.64 (m, 19H), 0.42 (dd, J=5.2, J$_2$=7.8, 1H) ppm.

The Removal of Protective Groups from the Glycoside

The obtained in previous step ester was treated with p-toluenesulfonic acid, according to procedure described in example 2. The purification of the crude product by silica gel column chromatography (elution with dichloromethane-methanol (96:4, v/v)) afforded desired saponin in 73% yield.

(20R)-21-O-Nonanoyl-20-methylpregn-5-ene-3β, 16β,17α,21-tetraol 16-O-{2-O-(4-methoxybenzoyl)-β-D-xylopyranosyl-(1→3)-2'-O-acetyl-α-L-arabinopyranoside} (compound 12)

IR(CHCl$_3$) ν=3590, 1728, 1606, 1512, 1259, 1170 cm$^{-1}$; $^1$H NMR (400 MHz, CDCl$_3$/MeOD, 25° C., TMS), δ=7.95 (d, J=8.9, 2H), 6.89 (d, J=8.9, 2H), 5.27 (m, 1H), 5.00 (dd, J=6.7, J$_2$=8.5, 1H), 4.88 (dd, J$_1$=7.0, J$_2$=7.8, 1H), 4.61 (d, J=6.7, 1H), 4.25 (d, J=6.6, 1H), 4.00-4.08 (m, 2H), 3.82-3.95 (m, 2H), 3.85 (m, 1H), 3.82 (s, 3H), 3.58-3.67 (m, 4H), 3.42 (m, 2H), 3.27-3.35 (m, 2H), 2.17 (t, J=−7.5, 2H), 1.67 (s, 3H), 1.22 (bs, 12H), 0.95 (s, 3H), 0.88 (d, J=7.0, 3H), 0.84 (t, J=6.6, 3H), 0.77 (s, 3H) ppm; $^{13}$C NMR (100 MHz, CDCl$_3$/MeOD, 25° C., TMS), δ=174.1 (C), 169.4 (C), 165.6 (C), 163.7 (C), 140.5 (C), 131.9 (2CH), 121.6 (C), 121.3 (CH), 113.6 (2CH), 102.3 (CH), 101.7 (CH), 88.3 (C), 86.6 (C), 79.6 (CH), 73.9 (CH), 73.1 (CH), 71.3 (CH), 70.4 (CH), 69.3 (CH), 68.2 (CH$_2$), 67.3 (CH), 64.6 (CH$_2$), 64.4 (CH$_2$), 55.3 (CH$_3$), 49.2 (CH), 48.4 (CH), 46.5 (C), 41.8 (CH$_2$), 37.1 (CH$_2$), 36.3 (C), 35.0 (CH$_2$), 34.3 (CH$_2$), 33.7 (CH), 32.3 (CH$_2$), 31.7 (CH$_2$), 31.64 (CH), 31.60 (CH$_2$), 31.2 (CH$_2$), 29.1 (CH$_2$), 29.0 (2CH$_2$), 24.8 (CH$_2$), 22.5 (CH$_2$), 20.4 (CH$_2$), 20.3 (CH$_3$), 19.2 (CH$_3$), 13.9 (CH$_3$), 12.7 (CH$_3$), 11.9 (CH$_3$) ppm; ESI-MS m/z (%) 967.6 (MNa$^+$); for C$_{51}$H$_{76}$O$_{16}$Na, calculated: 967.5031. found: 967.5059.

Example 13

Studies of Cytotoxic Activity of Novel Compounds Against Selected Tumor Cell Lines Cytotoxic activities of the novel compounds, obtained according to this invention, were tested in vitro against following cancer cell lines: T-lymphoblastic leukemia cell line CEM; breast carcinoma cell line MCF7, lung carcinoma cell line A549, cervical carcinoma cell line HeLa, malignant melanoma cell line G-361, osteosarcoma cell line HOS, human glioblastoma cell line T98, human colon carcinoma cells HCT 116 and normal human fibroblasts BJ. All cell lines were cultured in DMEM medium (Sigma, Mo., USA) supplemented with 10% fetal calf serum, 2 mM glutamine, 100 U/ml penicillin and 100 μg/ml streptomycin, at 37° C. in a fully humidified atmosphere containing 5% CO$_2$. Suspensions of these lines (ca. 1.0×10$^5$ cells/ml) were placed in 96-well microtitre plates and after 3 h of stabilization the tested compounds were added in serially diluted concentrations. Saponins were dissolved in dimethylsulfoxide (DMSO) before addition to cultures. Control cultures were treated with DMSO alone. The final concentration of DMSO in the reaction mixtures never exceeded 0.6%. Four-fold dilutions of the intended test concentration were added at time zero in 20 μl aliquots to the microtitre plate wells. Usually, each test compound was evaluated at six 4-fold dilutions and in routine testing; the highest well concentration was 50 μM, although this varied in a few cases, depending on the test compound. After 72 h of culture, the cells were incubated with Calcein AM solution (Molecular Probes) for 1 h. The fluorescence of viable cells was quantified using a Fluoroscan Ascent instrument (Microsystems). The percentage of surviving cells in each well was calculated from the equation IC$_{50}$= (OD$_{drug\ exposed\ well}$/mean OD$_{control\ wells}$)×100%. The IC$_{50}$ value, the drug concentration lethal to 50% of the tumour cells, was calculated from the obtained dose-response curves. The results obtained for selected compounds are shown in Table 1.

The novel compounds were screened against various tumor cells. The effectiveness of all compounds was in nanomolar to micromolar range. Simultaneously, all compounds were tested for cytotoxicity to normal human fibroblast BJ and proved substantially less toxic (3-360 times) than towards malignant cell lines. New OSW-1 analogues have stronger effect on some cancer cell lines than OSW-1 (e.g. malignant melanoma G-361, breast carcinoma MCF7, osteosarcoma HOS, glioblastoma T98 and colon carcinoma HCT 116).

More importantly, the novel compounds exhibit much lower cytotoxicity on normal human BJ fibroblasts, thus having much bigger therapeutic window.

TABLE 1

IC$_{50}$ (μM) values obtained from the Calcein AM assays with the tested cancer and normal cell lines; means ± SD obtained from three independent experiments performed in triplicate. OSW-1 was used as a positive control.

| Compound No. | Cell line, IC$_{50}$ (μM) | | | | |
|---|---|---|---|---|---|
| | CEM | MCF7 | G 361 | HeLa | HOS |
| OSW-1 aglycone | >50 | >50 | >50 | >50 | >50 |
| OSW-1 | 0.003 ± 0.00003 | 0.0544 ± 0.0002 | 1.0 ± 0.1 | 0.0034 ± 0.0003 | 8.2 ± 0.4 |

TABLE 1-continued

IC$_{50}$ (µM) values obtained from the Calcein AM assays with the tested cancer and normal cell lines; means ± SD obtained from three independent experiments performed in triplicate. OSW-1 was used as a positive control.

| | | | | | |
|---|---|---|---|---|---|
| 1 | 0.02 ± 0.001 | 0.6 ± 0.1 | 0.75 ± 0.08 | 0.2 ± 0.01 | |
| 2 | 0.07 ± 0.01 | 0.7 ± 0.1 | 1.66 ± 0.9 | 0.24 ± 0.06 | |
| 4 | 0.06 ± 0.01 | 0.5 ± 0.07 | 0.39 ± 0.06 | 0.17 ± 0.01 | |
| 5 | 0.01 ± 0.002 | 0.4 ± 0.04 | 1.28 ± 0.2 | 0.03 ± 0.002 | |
| 7 | 0.34 ± 0.04 | 0.84 ± 0.51 | 0.89 ± 0.09 | 1.94 ± 0.05 | |
| 9 | 0.016 ± 0.005 | 0.048 ± 0.022 | 0.03 ± 0.01 | 0.067 ± 0.002 | 2.7 ± 0.6 |
| 10 | 0.058 ± 0.001 | 0.195 ± 0.021 | 0.3 ± 0.1 | 0.435 ± 0.064 | |

| | Cell line, IC$_{50}$ (µM) | | | |
|---|---|---|---|---|
| Compound No. | A 549 | T98 | HCT116 | BJ |
| OSW-1 | | | | |
| aglycone | >50 | >50 | >50 | >50 |
| OSW-1 | 0.027 ± 0.003 | 0.07 ± 0.006 | 8.4 ± 0.5 | 0.0002 ± 0.0000 |
| 1 | 0.1 ± 0.05 | | | 0.3 ± 0.04 |
| 2 | 0.17 ± 0.04 | | | 0.1 ± 0.02 |
| 4 | 0.16 ± 0.04 | | | 0.5 ± 0.06 |
| 5 | 0.02 ± 0.005 | | | 0.6 ± 0.07 |
| 7 | 0.55 ± 0.2 | 0.94 ± 0.02 | | 0.23 ± 0.08 |
| 9 | 0.72 ± 0.07 | 0.028 ± 0.001 | 2.8 ± 0.4 | 0.083 ± 0.005 |
| 10 | 0.55 ± 0.18 | 0.21 ± 0.05 | | 0.080 ± 0.004 |

Example 14

Effect of Novel Compounds on Activity of Caspases-3/7 in Cancer Cells

Figure 4:
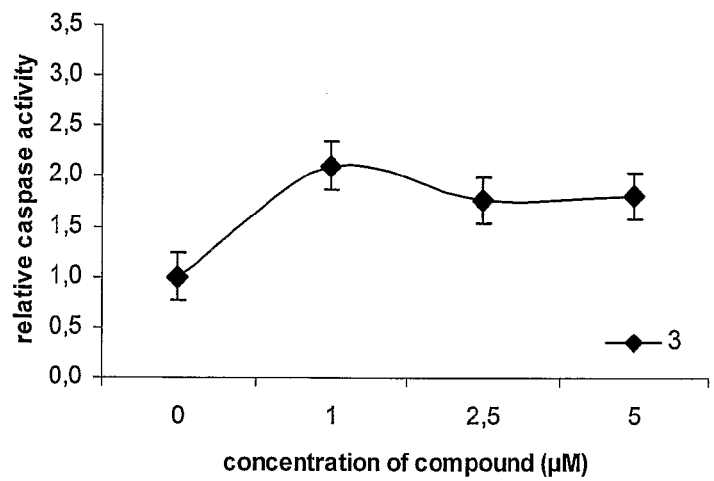
FIG. 4: Activity of caspases-3/7. Acute T-lymphoblastic leukemia cells CEM were treated by compounds 3, 6 and 7 compared with untreated control cells for 24 h. Data indicate the increase of relative caspases-3/7 activity.
Figure 4:
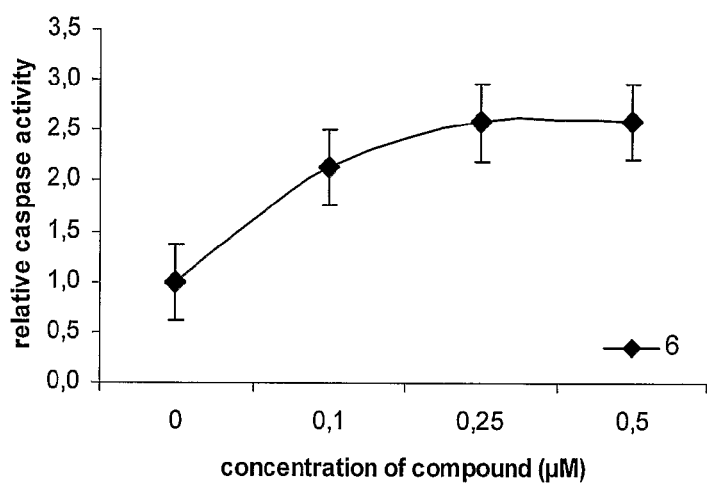
Figure 4:
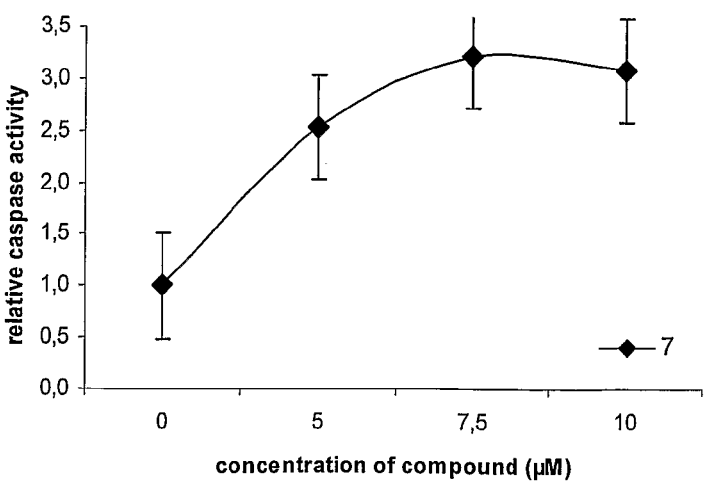

The CEM cells treated with the novel compounds were harvested by centrifugations and homogenized in an extraction buffer (10 mM KCl, 5 mM HEPES, 1 mM EDTA, 1 mM EGTA, 0.2% CHAPS, inhibitors of proteases, pH 7.4) on ice for 20 min. The homogenates were clarified by centrifugation at 10,000 g for 20 mM at 4° C., the proteins were quantified by the Bradford method and diluted to the same concentration. Lysates were then incubated for 1 h with 100 mM Ac-DEVD-AMC as a substrate (Sigma-Aldrich) in an assay buffer (25 mM PIPES, 2 mM EGTA, 2 mM MgCl$_2$, 5 mM DTT, pH 7.3). For negative controls, the lysates were supplemented with 100 mM Ac-DEVD-CHO as a caspase-3/7 inhibitor (Sigma-Aldrich). The fluorescence of the product was measured using a Fluoroskan Ascent microplate reader (Labsystems) at 346/442 nm (ex/em). Here, we determined the activity of caspase-3/7 in CEM cells exposed to 3, 6 or 7 using a fluorogenic substrate Ac-DEVD-AMC and/or caspase 3/7 inhibitor Ac-DEVD-DHO. Cells were treated in a dose-dependent manner with compounds 3 (1; 2.5; 5 µM), 6 (0.1; 0.25; 0.5 µM) and 7 (5; 7.5; 10 µM). Compound 7 induced the activity of caspase-3/7; after treatment for 24 h a threefold increase at 7.5 µM and 10 µM of the effector caspases was observed compared with the untreated control (FIG. 4). Compounds 3 and 6 affected the activity of caspases-3/7 a bit more weakly than 7; a twofold enhancement of the activity was detected after 24 h, and after treatment with higher concentrations the caspase-3/7 activity decreased.

Example 15

Novel Compounds Regulate Cell Cycle Progress and Apoptosis in Leukemia Cancer Cells The leukemia cancer CEM cells were trypsinized, seeded in 6 well plates, and immediately incubated with the respective compounds. After 48 h, the cells were again detached with trypsin, washed and stained overnight at 4° C. in 0.1% [m/v] sodium citrate, 0.1% [v/v] Triton X-100, and 50 µg/ml propidium iodide in PBS. DNA content was assessed with a flow cytometer (Cell Lab Quanta SC—MPL, Beckman Coulter, Calif., USA). In a histogram analysis, distribution of cells into the subG$_1$ ("apoptotic cells"), the G$_0$/G$_1$, S and the G$_2$/M peak was quantified using software MultiCycle AV (Phoenix Flow Systems, CA, USA).

Figure 2:
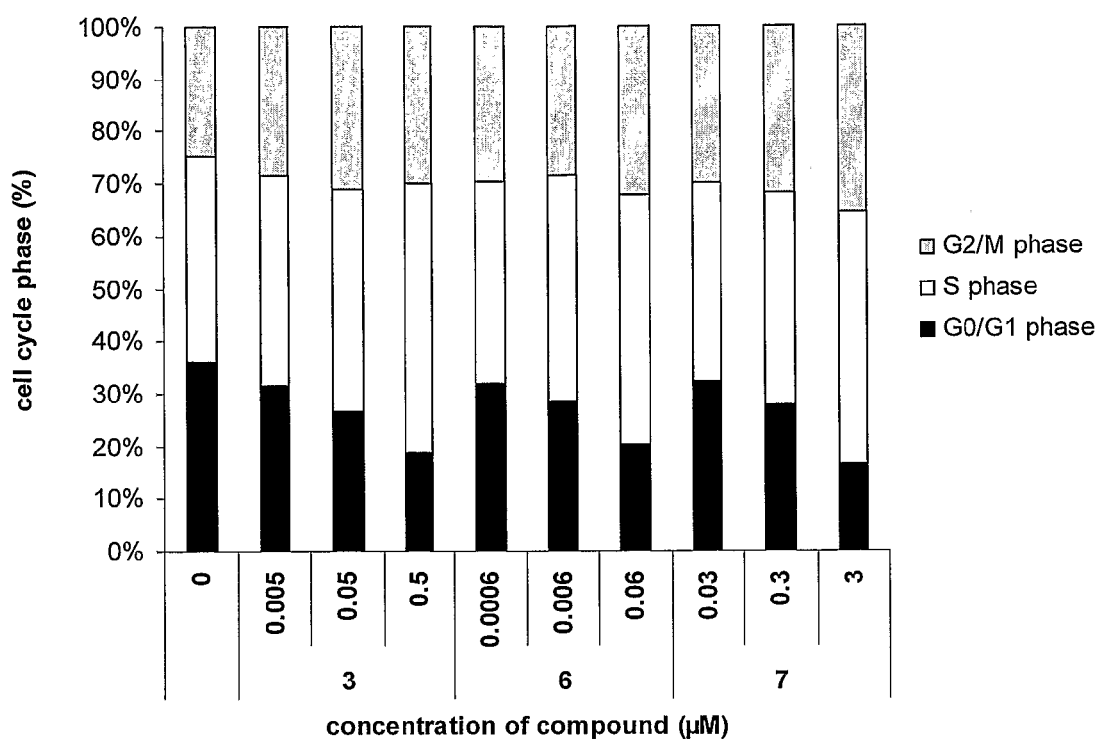
FIG. 2: Analysis of the cell cycle of CEM cells: untreated control compared with treated with 3, 6 and 7 using the flow cytometer. The graphs represent cells in the $G_1$, S, and $G_2$/M phases. Histograms of the treated cells were compared with control untreated cells. Data indicate percentage (%) of cells in respective phases.

Flow cytometry analysis was used to quantify the distribution of CEM cells in cell cycle phases including the subG$_1$ fraction of cells, as a marker of the number of apoptotic cells. We examined that treatment with 3, 6 and 7 increased the number of S-phase and G$_2$/M cells with concomitant decrease of G$_0$/G$_1$ cells in dose-dependent manner (FIG. 2). The portions of cells in S-phase and G$_2$/M are enhanced with increasing concentrations of compounds.

Figure 3:
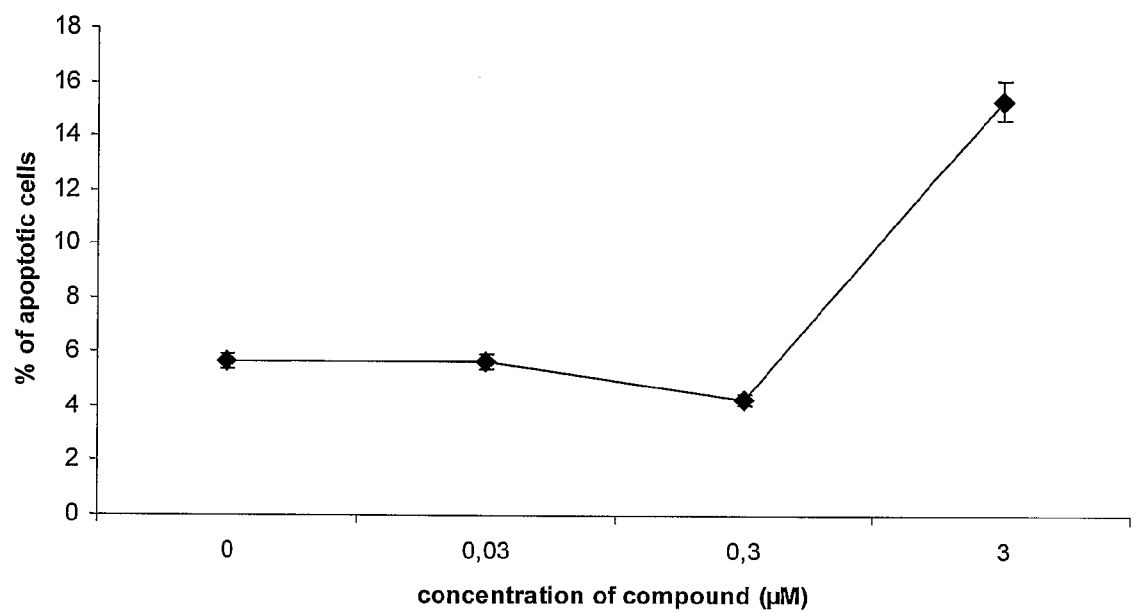
FIG. 3: Flow cytometric quantification of apoptosis (subG$_1$ peak) in CEM cells treated with compound 7 for 24 h. The subG$_1$ peak means apoptotic cells with a reduced DNA content. Three concentrations of compound were compared with untreated cells. The data shown are means±SD obtained from three independent experiments in triplicate.

We also found that treatment with 7 increased the amount of debris 3-fold compared with untreated controls after 24 h (FIG. 3). Therefore, these tested novel compounds were effective in causing a cell cycle arrest and inducing apoptosis.

TABLE 2

Cell cycle distribution of CEM cells after flow cytometry analysis.

| | Control/compound | Apoptosis | Cell cycle distribution | | |
|---|---|---|---|---|---|
| Cell line | (24 h) | subG$_1$ | G$_0$/G$_1$ | S | G$_2$/M |
| CEM | Control | 5% | 34% | 37% | 24% |
| | 3 (0.5 µM) | 11% | 17% | 46% | 26% |
| | 7 (3 µM) | 15% | 14% | 41% | 30% |

Histograms of the treated cells were compared with control untreated cells. The percentages indicate number of cells in subG$_1$ fraction and G$_0$/G$_1$, S, G$_2$/M phases of the cell cycle.

The flow cytometry analysis showed an increase in subG$_1$ phase of the cell cycle (apoptotic cells) in CEM cell line after treatment with saponin derivatives 3 or 7 (Table 4). Treatment of CEM cells with 3 and 7 increased number in subG$_1$ phase (FIG. 3), S and G$_2$/M phase with decrease in number of cells in G$_0$/G1 phase (FIG. 2).

Example 16

Western Blot Analysis of Pro- and Anti-Apoptotic Proteins in Leukemia Cancer Cells The cells were seeded in a density $2.2 \times 10^4$ cells/cm$^2$ using culture medium in 100-mm culture dishes. Immediately the cells were treated by novel saponins: 3 (1; 2.5; 5 μM), 6 (0.1; 0.25; 0.5 μM) and 7 (5; 7.5; 10 μM). DMSO was used as a vehicle for controls. After 24 h treatment, the cells were washed three times with cold PBS (10 mM, pH 7.4) and lysed in ice-cold protein extract RIPA buffer (20 mM Tris-HCl, pH 7.4, 5 mM EDTA, 2 mM EGTA, 100 mM NaCl, 2 mM NaF, 0.2% Nonidet P-40, 30 mM PMSF, 1 mM DTT, 10 mg/ml of aprotinin and leupeptin). The lysate was collected into microfuge tube and incubated on ice for 1 h. It was then cleared by centrifugation at 10,000×g for 30 mM at 4° C., and supernatant was collected, aliquoted, and stored at −80° C. Proteins in lysates were quantified by the Bradford method and then diluted with Laemmli electrophoresis buffer. Proteins were then separated on 10% or 12% SDS-polyacrylamide gels, transferred onto nitrocellulose membranes (Bio-Rad Laboratories, CA, USA) and stained with Ponceau S to check equal protein loading. The membranes were blocked with 5% (w/v) non-fat dry milk and 0.1% Tween-20 in PBS for 2 h and probed with the specific primary antibodies overnight. After washing in PBS and PBS with 0.1% Tween-20, the membranes were probed with horseradish peroxidase-conjugated secondary antibodies and visualized with chemiluminescent detection reagent West Pico Supersignal (Thermo Fisher Scientific, Rockford, USA). To confirm equal protein loading, immunodetection was performed with the anti-α-tubulin monoclonal antibody. The experiments were repeated three times. The protein expressions in treated cells were compared to untreated controls.

Figure 5:
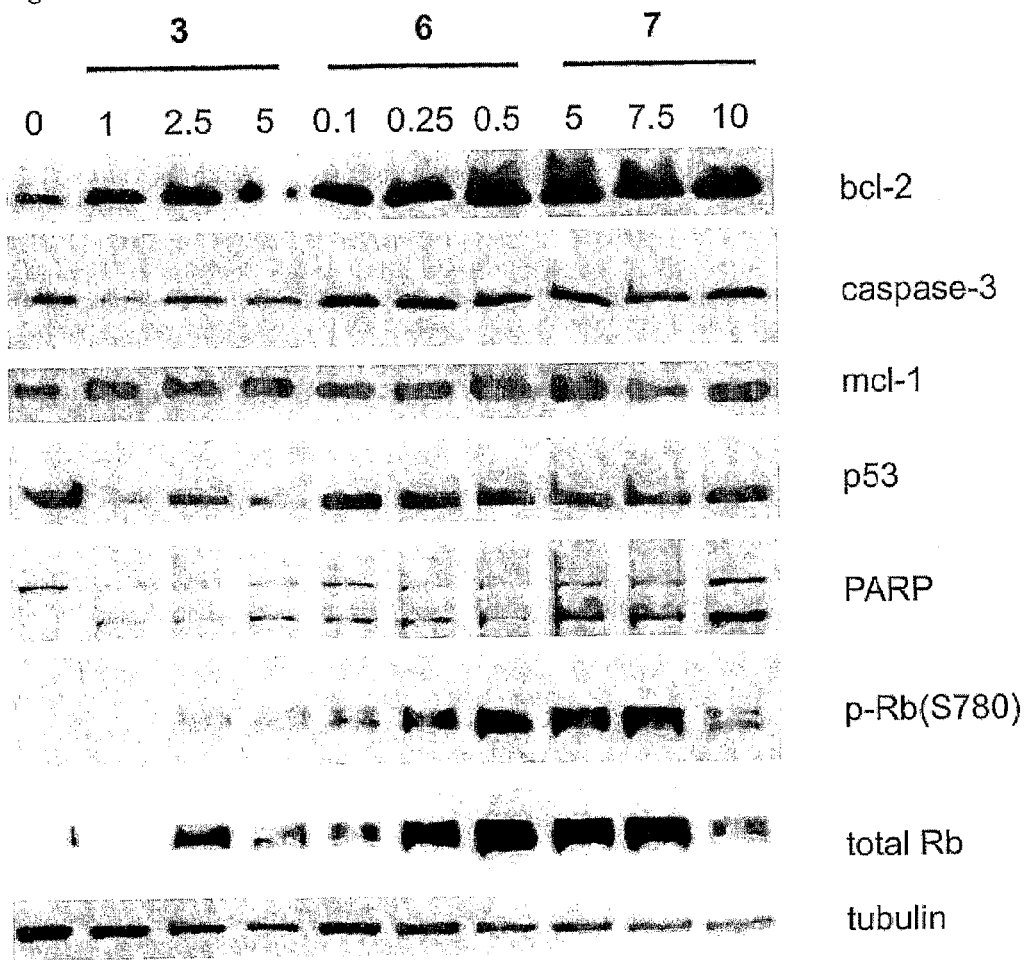
FIG. 5: Western blot analysis of apoptosis related proteins (pRb S780, Rb, PARP, Bcl-2, Mcl-1, p53, procasapase-3) in leukemia cells (CEM) treated by novel compounds. The protein expressions of treated cells by 3, 6 and 7 for 24 h in three different concentrations were compared with the protein expression of control, untreated cells. The expression of α-tubulin was used as a protein loading marker.
Figure 6:
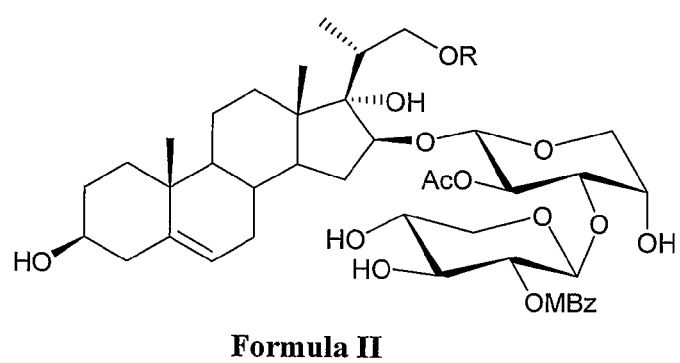
FIG. 6: General formula II.

Western blot analysis was used to detect changes in apoptosis related protein expression in leukemia cancer cell line. To monitor changes, we collected the cells after 24 h treatment with novel compounds. Changes in apoptosis related protein expression after treatment with saponin derivatives are shown in FIG. 5. Expression of a tumour suppressor protein p53 in controls of leukemia cancer cell line was observed and 6 and 7 caused its enhanced expression after 24 h. The protein expression increased strongly after treatment by 6 and 7 in dose-dependent manner. At the same concentrations and time of treatment, there was the increase of phosphorylation of pRb S780 observed, which is the inactive form of Rb protein. This enables the entrance in the S-phase of the cell cycle. This finding correlates with our flow cytometric analysis, which shows accumulation of cells in S-phase and $G_2/M$ phase. The antiapoptotic Bcl-2 protein increased after 6 and 7 treatment in dose-dependent manner (24 h). (FIG. 5)

It has been known that the execution mechanism of apoptosis is mediated by caspase cascade activation (Budihardjo et al., Annu. Rev. Cell Dev. Biol. 15, 269-290, 1999). Caspase-3 is an executioner protease that results in the cleavage of PARP and subsequent DNA degradation and apoptotic death (Allen et al., 1998, Cell. Mol. Life. Sci., 54, 427-445; Cain et al., 2002, Biochimie 84, 203-214). These results confirm that compounds 3, 6 and 7 can support apoptosis with caspase-3 activation (FIG. 4). In leukemia cancer cell line, Western blot analysis showed accumulation of caspase-3 and cleavage of PARP after 24 h treatment with compounds 3, 6 and 7 in dose-dependent manner (FIG. 5). These data therefore confirm that novel compounds induced apoptosis of mammalian cells in a concentration- and time-dependent manner.

Example 17

Dry Capsules 5000 capsules, each of which contains 0.25 g of one of the compounds of the formula II as active ingredient, are prepared as follows:
Composition

| Active ingredient | 1250 g |
| Talc | 180 g |
| Wheat starch | 120 g |
| Magnesium stearate | 80 g |
| Lactose | 20 g |

Preparation process: The powdered substances mentioned are pressed through a sieve of mesh width 0.6 mm. Portions of 0.33 g of the mixture are transferred to gelatine capsules with the aid of a capsule-filling machine.

Example 18

Soft Capsules 5000 soft gelatine capsules, each of which contains 0.05 g of one of the compounds of the formula II as active ingredient, are prepared as follows:
Composition

| Active ingredient | 250 g |
| Lauroglycol | 2 litres |

Preparation process: The powdered active ingredient is suspended in Lauroglykol® (propylene glycol laurate, Gattefossé S. A., Saint Priest, France) and ground in a wet-pulveriser to a particle size of about 1 to 3 μm. Portions of in each case 0.419 g of the mixture are then transferred to soft gelatine capsules by means of a capsule-filling machine.

Example 19

Soft Capsules 5000 soft gelatine capsules, each of which contains 0.05 g of one of the compounds of the formula II as active ingredient, are prepared as follows:
Composition

| Active ingredient | 250 g |
| PEG 400 | 1 litre |
| Tween 80 | 1 litre |

Preparation process: The powdered active ingredient is suspended in PEG 400 (polyethylene glycol of Mr between 380 and about 420, Sigma, Fluka, Aldrich, USA) and Tween® 80 (polyoxyethylene sorbitan monolaurate, Atlas Chem. Inc., Inc., USA, supplied by Sigma, Fluka, Aldrich, USA) and ground in a wet-pulveriser to a particle size of

The invention claimed is:
1. Compounds of formula II,

Formula II

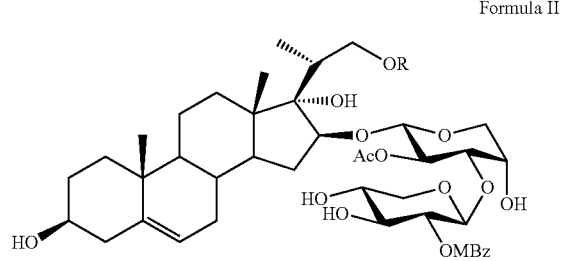

wherein
MBz denotes p-methoxybenzoyl, and
R is selected from the group consisting of $C_{6-10}$ aryl-$C_{1-4}$ alkyl-, $C_{1-18}$ alkanoyl, $C_{3-18}$ alkenoyl, $C_{6-10}$ aryl-C(O)—, $C_{6-10}$aryl-$C_{1-4}$alkyl-C(O)—, wherein each of the groups can optionally be substituted by one or more substituents selected from the group consisting of $C_{1-6}$ alkyl, $C_{1-6}$alkoxy, halogen, $C_{1-6}$ alkanoyl, $C_{1-6}$ alkenoyl, $C_{6-10}$ aryl-C(O)—, $C_{6-10}$ aryl, cyano, nitro and di($C_{1-6}$ alkyl)amino groups.

2. A method of preparation of the compounds of formula II according to claim 1, wherein R is $C_{6-10}$aryl-$C_{1-4}$alkyl- or substituted $C_{6-10}$aryl-$C_{1-4}$ alkyl-, wherein any substituted R group is substituted according to claim 1, characterized in that it comprises the following steps:
a) Williamson etherification of the primary 22-hydroxyl group of (20R)-20-methyl-6β-methoxy-3α,5α-cyclo-pregnane-16β,17α,21-triol of formula III Formula III

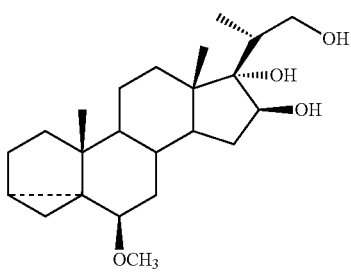

with a corresponding benzyl halide or substituted benzyl halide in the presence of a base in an etheric solvent;
b) glycosylation of the steroidal aglycone obtained as described in step (a) with a disaccharide donor of formula IV Formula IV

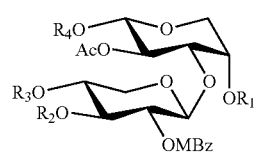

wherein $R_1$, $R_2$, $R_3$ are protective groups for alcohols and $OR_4$ is a leaving group;
c) removal of the protective groups from the obtained glycoside with an acidic catalyst.

3. A method of preparation of the compounds of formula II according to claim 1, wherein R is $C_{1-18}$ alkanoyl, $C_{3-18}$ alkenoyl, $C_{6-10}$aryl-C(O)—, $C_{6-10}$aryl-$C_{1-4}$alkyl-C(O)—, substituted $C_{1-18}$ alkanoyl, substituted $C_{3-18}$ alkenoyl, substituted $C_{6-10}$ aryl-C(O)—, substituted $C_{6-10}$ aryl-$C_{1-4}$ alkyl-C(O)—, wherein any substituted R group is substituted according to claim 1, characterized in that it comprises the following steps:
a) selective protection of the primary 22-hydroxyl group of (20R)-20-methyl-6β-methoxy -3α,5α-cyclopregnane-16β,17α,21-triol of formula III;

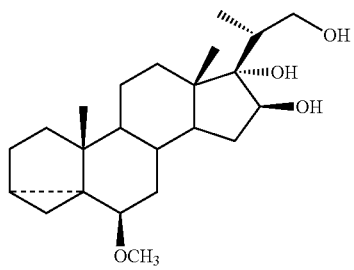

b) glycosylation of the steroidal aglycone obtained as described in step (a) with a glycosyl donor of formula IV

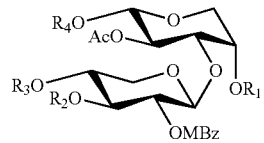

wherein $R_1$, $R_2$, $R_3$ are protective groups for alcohols and $OR_4$ is a leaving group;
c) selective deprotection of the primary 22-hydroxyl group of the obtained glycoside;
d) esterification of the primary alcohol with a corresponding carboxylic acid or a corresponding carboxylic acid derivative;
e) removal of the protective groups from the obtained glycoside using an acidic catalyst.

4. The compounds of formula II according to claim 1 for use as medicaments.

5. The compounds of formula II according to claim 1 for use in the treatment of cancer.

6. A pharmaceutical composition, characterized in that it comprises one or more derivatives of the general formula II according to claim 1 or pharmaceutically acceptable salt or addition salt thereof, and one or more excipients.

7. The pharmaceutical composition according to claim 6, further containing a cytostatic.

8. The pharmaceutical composition according to claim 7, wherein the cytostatic is selected from the group consisting of cyclophosphamid, 5-fluorouracil, adriamycin, mitoxantrone, mitomycin, camptothecin, cisplatin, methotrexate, taxol, and doxorubicin.

9. Compounds according to claim 1, wherein R is selected from the group consisting of $C_{6-10}$ aryl-$C_{1-4}$ alkyl-, $C_{1-18}$ alkanoyl, $C_{3-18}$ alkenoyl, $C_{6-10}$ aryl-C(O)—, $C_{6-10}$ aryl-$C_{1-4}$ alkyl-C(O)—, wherein each of the groups is substituted by one to three substituents selected from the group consisting of $C_{1-6}$ alkyl, $C_{1-6}$ alkoxy, halogen, $C_{1-6}$ alkanoyl, $C_{1-6}$ alkenoyl, $C_{6-10}$ aryl-C(O)—, $C_{6-10}$ aryl, cyano, nitro, and di($C_{1-6}$alkyl) amino groups.

10. A compound of formula II according to claim 1, wherein the compound is part of a medicament for use in treating cancer.

11. A method of at least one of inhibiting cell proliferation and inducing apoptosis in cells, the method comprising administering a compound of formula II according to claim 1.

12. The method of at least one of inhibiting cell proliferation and inducing apoptosis in cells of claim 11, wherein the compound of formula II according to claim 1 is administered to a human patient.

13. The method of at least one of inhibiting cell proliferation and inducing apoptosis in cells of claim 11, wherein the compound of formula II according to claim 1 is administered to a human patient to treat cancer.

14. The method of at least one of inhibiting cell proliferation and inducing apoptosis in cells of claim 11, wherein the compound of formula II according to claim 1 is administered to a human patient to treat cancer, wherein the cancer is leukemia.

15. The method of at least one of inhibiting cell proliferation and inducing apoptosis in cells of claim 11, wherein the compound of formula II according to claim 1 is administered as a cell culture additive.

16. A compound of formula II according to claim 1, wherein the compound is part of a capsule dosage form.

* * * * *